United States Patent
Charles et al.

(10) Patent No.: US 9,839,678 B2
(45) Date of Patent: *Dec. 12, 2017

(54) HUMAN TISSUE KALLIKREIN 1 GLYCOSYLATION ISOFORMS

(71) Applicant: DiaMedica Inc., Winnipeg (CA)

(72) Inventors: Matthew Charles, St. Louis Park, MN (US); Tadeusz Kolodka, Plymouth, MN (US); Mark Williams, Plymouth, MN (US)

(73) Assignee: DIAMEDICA INC., Winnipeg (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,126

(22) Filed: May 12, 2016

(65) Prior Publication Data

US 2017/0119862 A1 May 4, 2017

Related U.S. Application Data

(63) Continuation of application No. 14/677,122, filed on Apr. 2, 2015, now Pat. No. 9,364,521, which is a continuation of application No. 13/909,220, filed on Jun. 4, 2013, now abandoned.

(60) Provisional application No. 61/789,978, filed on Mar. 15, 2013, provisional application No. 61/655,388, filed on Jun. 4, 2012.

(51) Int. Cl.
| | | |
|---|---|---|
| *A61K 38/48* | (2006.01) | |
| *A61P 3/10* | (2006.01) | |
| *C12N 9/96* | (2006.01) | |
| *C12N 9/64* | (2006.01) | |

(52) U.S. Cl.
CPC ........ *A61K 38/4853* (2013.01); *C12N 9/6445* (2013.01); *C12N 9/96* (2013.01); *C12Y 304/21035* (2013.01)

(58) Field of Classification Search
None
See application file for complete search history.

(56) References Cited

U.S. PATENT DOCUMENTS

| | | |
|---|---|---|
| 3,472,931 A | 10/1969 | Stoughton |
| 3,527,864 A | 9/1970 | MacMillan et al. |
| 3,896,238 A | 7/1975 | Smith |
| 3,903,256 A | 9/1975 | MacMillan et al. |
| 3,952,099 A | 4/1976 | Smith |
| 4,046,886 A | 9/1977 | Smith |
| 4,130,643 A | 12/1978 | Smith |
| 4,130,667 A | 12/1978 | Smith |
| 4,146,613 A | 3/1979 | Dietze et al. |
| 4,150,121 A | 4/1979 | Dietze et al. |
| 4,299,826 A | 11/1981 | Luedders |
| 4,315,988 A | 2/1982 | Miwa et al. |
| 4,335,115 A | 6/1982 | Thompson et al. |
| 4,343,798 A | 8/1982 | Fawzi |
| 4,379,454 A | 4/1983 | Campbell et al. |
| 4,405,616 A | 9/1983 | Rajadhyaksha |
| 4,439,196 A | 3/1984 | Higuchi |
| 4,447,224 A | 5/1984 | DeCant, Jr. et al. |
| 4,447,233 A | 5/1984 | Mayfield |
| 4,474,893 A | 10/1984 | Reading |
| 4,475,196 A | 10/1984 | LaZor |
| 4,486,194 A | 12/1984 | Ferrara |
| 4,487,603 A | 12/1984 | Harris |
| 4,666,828 A | 5/1987 | Gusella |
| 4,676,980 A | 6/1987 | Segal et al. |
| 4,683,202 A | 7/1987 | Mullis |
| 4,689,042 A | 8/1987 | Sarnoff et al. |
| 4,746,515 A | 5/1988 | Cheng et al. |
| 4,788,062 A | 11/1988 | Gale et al. |
| 4,801,531 A | 1/1989 | Frossard |
| 4,816,567 A | 3/1989 | Cabilly et al. |
| 4,820,720 A | 4/1989 | Sanders et al. |
| 4,835,253 A | 5/1989 | Burton |
| 4,863,738 A | 9/1989 | Taskovich |
| 4,863,970 A | 9/1989 | Patel et al. |
| 4,925,678 A | 5/1990 | Ranney |
| 4,959,217 A | 9/1990 | Sanders et al. |
| 5,124,322 A | 6/1992 | Hughes |
| 5,167,616 A | 12/1992 | Haak et al. |
| 5,169,383 A | 12/1992 | Gyory et al. |
| 5,187,305 A | 2/1993 | Thompson et al. |
| 5,192,659 A | 3/1993 | Simons |
| 5,223,409 A | 6/1993 | Ladner et al. |

(Continued)

FOREIGN PATENT DOCUMENTS

| | | |
|---|---|---|
| CA | 2415392 A1 | 1/2002 |
| CA | 2465632 A1 | 5/2003 |
| CA | 2659012 | 1/2008 |
| CN | 1384199 | 12/2002 |
| CN | 101255438 | 9/2008 |
| DE | 4420523 A1 | 12/1995 |
| DE | 102008003566 | 7/2009 |
| DE | 102008003568 | 7/2009 |
| EP | 0368187 | 9/1993 |
| EP | 0419504 | 1/1994 |

(Continued)

OTHER PUBLICATIONS

Xia et al., "Kallikrein Protects Against Ischemic Stroke by Inhibiting Apoptosis and Inflammation and Promoting Angiogenesis and Neurogenesis," Human Gene Ther. 17:206-219 (2006).*
Shi et al., "Tissue Kallikrein Alleviates Cerebral Ischemia-Reperfusion Injury by Activating the B2R-ERK1/2-CREB-Bcl-2 Signaling Pathway in Diabetic Rats," Oxidative Medicine and Cellular Longevity, pp. 1-14 (2016).*
International Search Report and Written Opinion for International Application No. PCT/US2012/036556, dated Aug. 30, 2012.
Supplementary European Search Report for European Application No. 13801165.5, dated Feb. 8, 2016, 5 pages.

(Continued)

*Primary Examiner* — Julie Ha
*Assistant Examiner* — Kristina M Hellman

(57) ABSTRACT

Provided are preparations of tissue kallikrein-1 (KLK1) glycoforms having a defined number of oligosaccharide units per KLK1 molecule. Also provided are mixtures of such glycoforms, pharmaceutical compositions containing such glycoforms or mixtures thereof, methods of obtaining the rhKLK1 glycoforms, and therapeutic uses thereof.

14 Claims, 9 Drawing Sheets

(56) References Cited

U.S. PATENT DOCUMENTS

| | | |
|---|---|---|
| 5,225,182 A | 7/1993 | Sharma |
| 5,234,956 A | 8/1993 | Lipton |
| 5,253,785 A | 10/1993 | Haber et al. |
| 5,262,430 A | 11/1993 | Borrevang et al. |
| 5,272,057 A | 12/1993 | Smulson et al. |
| 5,370,862 A | 12/1994 | Klokkers-Bethke et al. |
| 5,378,730 A | 1/1995 | Lee et al. |
| 5,403,484 A | 4/1995 | Ladner et al. |
| 5,403,486 A | 4/1995 | Leung |
| 5,462,739 A | 10/1995 | Dan et al. |
| 5,478,323 A | 12/1995 | Westwood et al. |
| 5,516,639 A | 5/1996 | Tindall et al. |
| 5,534,615 A | 7/1996 | Baker et al. |
| 5,561,165 A | 10/1996 | Lautt et al. |
| 5,571,698 A | 11/1996 | Ladner et al. |
| 5,580,576 A | 12/1996 | Veronesi et al. |
| 5,614,192 A | 3/1997 | Vandenbark |
| 5,648,095 A | 7/1997 | Illum et al. |
| 5,698,738 A | 12/1997 | Garfield et al. |
| 5,716,617 A | 2/1998 | Khandke et al. |
| 5,744,487 A | 4/1998 | Ohshima et al. |
| 5,762,922 A | 6/1998 | Noble et al. |
| 5,789,447 A | 8/1998 | Wink, Jr. et al. |
| 5,874,531 A | 2/1999 | Strominger et al. |
| 5,902,829 A | 5/1999 | Schneider et al. |
| 5,906,987 A | 5/1999 | Chwalisz et al. |
| 5,910,316 A | 6/1999 | Keefer et al. |
| 5,958,427 A | 9/1999 | Salzman et al. |
| 5,980,896 A | 11/1999 | Hellstrom et al. |
| 6,165,975 A | 12/2000 | Adams et al. |
| 6,171,232 B1 | 1/2001 | Papandreou et al. |
| 6,221,633 B1 | 4/2001 | Ertl et al. |
| 6,277,558 B1 | 8/2001 | Hudson |
| 6,288,040 B1 | 9/2001 | Muller et al. |
| 6,303,606 B1 | 10/2001 | Leonardi et al. |
| 6,307,027 B1 | 10/2001 | Linemeyer et al. |
| 6,358,536 B1 | 3/2002 | Thomas |
| 6,369,071 B1 | 4/2002 | Haj-Yehia |
| 6,436,996 B1 | 8/2002 | Vitek et al. |
| 6,492,405 B2 | 12/2002 | Haj-Yehia |
| 6,586,438 B2 | 7/2003 | Piper |
| 6,887,872 B2 | 5/2005 | Literati Nagy et al. |
| 6,962,793 B2 | 11/2005 | Diamandis |
| 7,087,247 B2 | 8/2006 | Li et al. |
| 7,195,759 B2 | 3/2007 | Sabbadini et al. |
| 7,622,447 B2 | 11/2009 | Lautt et al. |
| 7,723,326 B2 | 5/2010 | Lagu et al. |
| 8,058,019 B2 | 11/2011 | Roggenbuck |
| 9,364,521 B2 | 6/2016 | Charles et al. |
| 2001/0056068 A1 | 12/2001 | Chwalisz et al. |
| 2002/0106368 A1 | 8/2002 | Bot et al. |
| 2002/0192723 A1 | 12/2002 | Yoo |
| 2003/0045553 A1 | 3/2003 | Bussolari et al. |
| 2003/0114469 A1 | 6/2003 | Cohen |
| 2003/0158090 A1 | 8/2003 | Pedersen-Bjergaard et al. |
| 2003/0166662 A1 | 9/2003 | Fryburg et al. |
| 2003/0181461 A1 | 9/2003 | Lautt et al. |
| 2003/0216306 A1 | 11/2003 | Sabbadini et al. |
| 2003/0235609 A1 | 12/2003 | Lautt |
| 2004/0068005 A1 | 4/2004 | Szilvassy et al. |
| 2004/0151785 A1 | 8/2004 | Lautt |
| 2004/0209849 A1 | 10/2004 | Fischer |
| 2004/0253226 A1 | 12/2004 | Holaday et al. |
| 2005/0049293 A1 | 3/2005 | Lautt |
| 2007/0009438 A1 | 1/2007 | Lautt |
| 2007/0224209 A1 | 9/2007 | Berczi et al. |
| 2007/0238762 A1 | 10/2007 | Lautt |
| 2008/0004432 A1 | 1/2008 | Ruben et al. |
| 2009/0162342 A1 | 6/2009 | Berczi et al. |
| 2009/0233995 A1 | 9/2009 | Lautt |
| 2009/0324701 A1 | 12/2009 | Williams |
| 2010/0008899 A1 | 1/2010 | Williams |
| 2010/0226910 A1 | 9/2010 | Williams |
| 2011/0150781 A1 | 6/2011 | Charles et al. |
| 2012/0070425 A1 | 3/2012 | Williams et al. |
| 2012/0201804 A1 | 8/2012 | Williams et al. |
| 2012/0225051 A1 | 9/2012 | Williams |
| 2012/0276019 A1 | 11/2012 | Charles et al. |
| 2013/0089564 A1 | 4/2013 | Berczi et al. |
| 2013/0224230 A1 | 8/2013 | Berczi et al. |
| 2013/0280235 A1 | 10/2013 | Williams |
| 2013/0315891 A1 | 11/2013 | Charles et al. |
| 2013/0323222 A1 | 12/2013 | Charles et al. |
| 2014/0134152 A1 | 5/2014 | Willimas et al. |
| 2015/0196624 A1 | 7/2015 | Charles et al. |
| 2016/0000704 A1 | 1/2016 | Charles |

FOREIGN PATENT DOCUMENTS

| | | |
|---|---|---|
| EP | 0214826 | 10/1994 |
| EP | 0297913 | 2/1995 |
| EP | 0383472 | 2/1996 |
| EP | 0375437 | 9/1998 |
| EP | 0678522 | 1/2002 |
| EP | 0835139 | 9/2003 |
| EP | 0885961 | 12/2004 |
| GB | 1572146 | 7/1980 |
| JP | S53-86042 | 7/1978 |
| JP | 56-115715 | 9/1981 |
| JP | 57-114512 | 7/1982 |
| WO | WO 89/00192 | 1/1989 |
| WO | WO 89/10937 | 11/1989 |
| WO | WO 91/17767 | 11/1991 |
| WO | WO 92/00321 | 1/1992 |
| WO | WO 00/07575 | 2/2000 |
| WO | WO 00/19992 | 4/2000 |
| WO | WO 00/53776 | 9/2000 |
| WO | WO 01/02039 | 1/2001 |
| WO | WO 01/36611 | 5/2001 |
| WO | WO 02/13798 | 2/2002 |
| WO | WO 03/028730 | 4/2003 |
| WO | WO 2004/029238 | 4/2004 |
| WO | WO 2004/058258 | 7/2004 |
| WO | WO 2005/022146 | 3/2005 |
| WO | WO 2005/022164 | 3/2005 |
| WO | WO 2006/008002 | 1/2006 |
| WO | WO 2006/017538 | 2/2006 |
| WO | WO 2008/011713 | 1/2008 |
| WO | WO 2008/016883 | 2/2008 |
| WO | WO 2009/012571 | 1/2009 |
| WO | WO 2009/039704 | 4/2009 |
| WO | WO 2010/009557 | 1/2010 |
| WO | WO 2010/080833 | 7/2010 |
| WO | WO 2010/108262 | 9/2010 |
| WO | WO 2010/121358 | 10/2010 |
| WO | WO 2010/121361 | 10/2010 |
| WO | WO 2012/075342 | 6/2012 |
| WO | WO 2012/154574 | 11/2012 |
| WO | WO 2013/173923 | 11/2013 |
| WO | WO 2013/181755 | 12/2013 |
| WO | WO 2014/059536 | 4/2014 |

OTHER PUBLICATIONS

Supplementary European Search Report for European Application No. EP 07784988.3, dated Sep. 17, 2009.
International Search Report and Written Opinion for International Application No. PCT/CA2007/001321, dated Nov. 30, 2007.
International Preliminary Report on Patentability for International Application No. PCT/CA2007/001321, dated Jan. 27, 2009.
Supplemental European Search Report for European Application No. 10755352.1, dated Nov. 13, 2012.
International Search Report and Written Opinion for International Application No. PCT/CA2010/000413, dated Jun. 7, 2010.
International Preliminary Report on Patentability for International Application No. PCT/CA2010/000413, dated Sep. 27, 2011.
Abdelaziz, A. et al., "Glucose homeostasis in the nonobese diabetic mouse at the prediabetic stage," Endocrinology, 139:1115-1124 (1998).
Abdelhaleem et al., "Identification of immunosuppressive fractions from the rat submandibular salivary gland," Immunology (1992) 76:331-337.

(56) References Cited

OTHER PUBLICATIONS

Adams, D. H. et al., "Transforming growth factor-β induces human T lymphocyte migration in vitro," The Journal of Immunology, Jul. 15, 1991;147(2):609-612.

Albertini, R. et al., "Kallikrein-kinin system in one- and two-kidney Goldblatt hypertensive rats," Clinical Science (Lond)., Mar. 1979;56(3):227-233.

Alhenc-Gelas et al., "Measurement of urinary kallikrein activity: Species differences in kinin production," Biochimica et Biophysica Acta (1981) 677:477-488.

Allen et al., "Rapid onset synovial inflammation and hyperplasia induced by transforming growth factor β," The Journal of Experimental Medicine, (1990) 171:231-247.

Angermann et al., "Purification and characterization of human salivary-gland prokallikrein from recombinant baculovirus-infected insect cells," Eur. J. Biochem. (1992) 206:225-233.

Assan et al., "Metabolic and Immunological Effects of Cyclosporin in Recently Diagnosed Type 1 Diabetes Mellitus," The Lancet, p. 67-71, Jan. 12, 1995.

Atkinson et al., "Islet Cell Autoantigens in Insulin-Dependent Diabetes," Adkinson and Maclaren, Islet Cell Autoangtigens in Diabetes, J Clin Invest 92, p. 1608-1616, 1993.

Atkinson, M. A. et al, "Type 1 diabetes: New perspectives on disease pathogenesis and treatment," Lancet 2001; 358:221-229.

Auger, I. et al., "New autoantigens in rheumatoid arthritis (RA): screening 8268 protein arrays with sera from patients with RA," Annals of the Rheumatic Diseases, 68:591-594 (2009).

Baggio, L. L. et al., "A recombinant human glucagon-like peptide (GLP)-1-albumin protein (albugon) mimics peptidergic activation of GLP-1 receptor-dependent pathways coupled with satiety, gastrointestinal motility, and glucose homeostasis," Diabetes, 53:2492-2500 (2004).

Barnett et al., "Treatment of rheumatoid arthritis with oral Type II Collagen," Arthritis & Rheumatism (1998) 41(2):290-297.

Baumgarten et al., "Concentrations of glandular kallikrein in human nasal secretions increase during experimentally induced allergic rhinitis," The Journal of Immunology (1986) 137:1323-1328.

Benson et al., "Oral administration of myelin basic protein is superior to myelin in suppressing established relapsing experimental autoimmune encephalomyelitis," The Journal of Immunology, 162:6247-6254 (1999).

Berczi et al., "The influence of pituitary hormones on adjuvant arthritis," Arthritis and Rheumatism (1984) 27(6):682-688.

Bhoola et al., "Bioregulation of kinins: Kallikreins, kininogens, and kininases," Pharmacological Reviews, 44(1):1-80 (1992).

Biosis Database [Online], Biosciences Information Service, Philadelphia, PA, Tschoepe Carsten et al., "Transgenic expression of human kallikrein prevents altered left ventricular function, the decline in sarcoplasmic reticulum calcium pump activity and the rise in cardiac collagen content in diabetic rats," Database accession No. PREV200100068837, Circulation, 102(18):II.267 (Oct. 31, 2000).

Bindseil et al., "Pure compound libraries; a new perspective for natural product based drug discovery," Drug Discovery Today, 6(16):840-847 (2001).

Blaukat, A. et al., "Regulation of Cardiovascular Signaling by Kinins and Products of Similar Converting Enzyme Systems— Downregulation of bradykinin B2 receptor in human fibroblasts during prolonged agonist exposure," American Journal of Physiology, Heart and Circulatory Physiology, 284(6):H1909-H1916 (2003).

Bodin et al., "Kallikrein protects against micro albuminuria in experimental type I diabetes," Kidney International, 76(4):395-403 (2009).

Brandes et al., "Type I transforming growth factor-β receptors on neutrophils mediate chemotaxis to transforming growth factor-β," The Journal of Immunology (1991) 147(5):1600-1606.

Caperuto et al., "Modulation of bone morphogenetic protein-9 expression and processing by insulin, glucose, and glucocorticoids: possible candidate for hepatic insulin-sensitizing substance," Endocrinology, 149(12):6326-6335 (2008).

Carlson, M. W. et al., "Chronic ulcerative stomatitis: evidence of autoimmune pathogenesis," Oral Surgery, Oral Medicine, Oral Pathology, Oral Radiology, and Endodontology, 111:742-748 (2011).

Swant, Catalog listing for Monoclonal anti Rat Renin (118), [online], [Retrieved on Jan. 31, 2005], [Retrieved from the Internet: URL: http://www.swant.com/Antibodies_renin.htm, 1 page.

Chao, J. et al., "Experimental therapy with tissue kallikrein against cerebral ischemia," Frontiers in Bioscience, 11:1323-1327 (2006).

Chen et al., "Beneficial effects of kallikrein-binding protein in transgenic mice during endotoxic shock," Life Sciences (1997) 60(17):1431-1435.

Christensen, M. et al., "Lixisenatide, a novel GLP-1 receptor agonist for the treatment of type 2 diabetes mellitus," IDrugs, 12(8):503-513 (2009).

Christiansen et al., "Detection of tissue kallikrein in the bronchoalveolar lavage fluid of asthmatic subjects," J. Clin. Invest. (1987) 79:188-197.

Clements, J. et al., "The expanded human kallikrein (KLK) gene family: Genomic organization, tissue-specific expression and potential functions," Biological Chemistry, 382(1):5-14 (2001).

Clements, J. A., "The human kallikrein gene family: a diversity of expression and function," Molecular and Cellular Endocinology, 99:C1-C6 (1994).

Coker et al., "Role of hepatic α- and β-adrenergic receptor stimulation on hepatic glucose production during heavy exercise," American Journal of Physiology, Endocrinology and Metabolism, 273:E831-E838 (1997).

Croxatto, H. R. et al., "Inhibition of urinary kallikrein excretion by semi-purified renin in the rat," Clinical Science, 57:243s-245s (1979).

Cull et al., "Screening for receptor ligands using large libraries of peptides linked to C terminus of the lac repressor," PNAS, 89:1865-1869 (1992).

Cwirla et al., "Peptides on phage: A vast library ofpeptides for identifying ligands," Proc. Natl. Acad. Sci. USA, 87:6378-6382 (1990).

Damas, J. et al., "The kallikrein-kinin system, angiotensin converting enzyme inhibitors and insulin sensitivity," Diabetes/Metabolism Research and Reviews, 20(4):288-297 (2004).

Dertzbaugh et al., "Comparative effectiveness of cholera toxin B subunit and alkaline phosphatase as carriers for oral vaccines," Infection and Immunity (1993) 61(1):48-55.

Devlin et al., "No excess of homozygosity at loci used for DNA fingerprinting," Science, 249 (4975):1416-1420 (1990).

DeWitt et al., "'Diversomers': An approach to nonpeptide, nonoligomeric chemical diversity," Proc. Natl. Acad. Sci. USA, 90:6909-6913 (1993).

Dodge, G. R. et al., "Immunohistochemical detection and immunochemical analysis of type II collagen degradation in human normal, rheumatoid, and osteoarthritic articular cartilages and in explants of bovine articular cartilage cultured with interleukin 1," J. Clin. Invest., 83:647-661 (1989).

Dong, Y. et al., "Tissue-specific promoter utilisation of the kallikrein-related peptidase genes, KLK5 and KLK7, and cellular localisation of the encoded proteins suggest roles in exocrine pancreatic function," Biological Chemistry, 389(2):99-109 (Feb. 2008).

Doyle, B. L. et al., "Biophysical signatures of noncovalent aggregates formed by a glucagonlike peptide-1 analog: a prototypical example of biopharmaceutical aggregation," J. Pharm. Sci., 94(12):2749-2763 (2005).

Dunbar et al., "Central Adrenergic Suppression Augments the Insulin and Glucagon Secretory, and the Glycogenolytic Responses in Streptozotocin-Diabetic Rats," Hormone Research, 36:80-85 (1991).

Ebringer, A et al., "'B27 Disease' Is a New Autoimmune Disease That Affects Millions of People," Annals of the New York Academy of Sciences, 1110:112-120 (2007).

(56) References Cited

OTHER PUBLICATIONS

Eldefrawi et al., "Purification and molecular properties of the acetylcholine receptor from Torpedo Electroplax," Archives of Biochemistry and Biophysics, (1973) 159:362-373.
Ellingsgaard et al., "Interleukin-6 regulates pancreatic alpha-cell mass expansion," PNAS USA, 105(35):13163-13168 (Sep. 2008), Published online Aug. 21, 2008, doi: 10.1073/pnas.0801059105.
Emami, N. et al., Utility of kallikrein-related peptidases (KLKs) as cancer biomarkers, Clinical Chemistry, 54(10):1600-1607 (2008).
Emanueli, C. et al., "Prophylactic Gene Therapy With Human Tissue Kallikrein Ameliorates Limb Ischemia Recovery in Type 1 Diabetic Mice," Diabetes, 53:1096-1103 (Apr. 2004).
Erb et al., "Recursive deconvolution of combinatorial chemical libraries," Proc. Natl. Acad. Sci. USA, 91:11422-11426 (1994).
Ericson et al., "Studies on the sicca syndrome in patients with rheumatoid arthritis," Acta. Rheum. Scand. (1970) 16: 60-80.
Weiner, H. L. et al.,"Oral tolerance," Immunol. Rev., 206:232-259 (Aug. 2005).
Fava et al., "Transforming growth factor β1 (TGF-β1) induced neutrophil recruitment to synovial tissues: Implications for TGF-β-driven synovial inflammation and hyperplasia," The Journal of Experimental Medicine, (1991) 173:1121-1132.
Felici, F., "Selection of antibody ligands from a large library of oligopeptides expressed on a multivalent exposition vector," J. Mol. Biol., 222:301-310 (1991).
Felson et al., "American College of Rheumatology preliminary definition of improvement in rheumatoid arthritis," Arthritis & Rheumatism (1995) 38(6): 727-735.
Ferreira et al., "Nitric oxide modulates eosinophil infiltration in antigen-induced airway inflammation in rats," European Journal of Pharmacology (1998) 358: 253-259.
Ferretti et al., "Intracolonic release of nitric oxide during trinitrobenzene sulfonic acid rat colitis," Digestive Dieseases and Sciences (1997) 42(12): 2606-2611.
Feutren et al., "Cyclosporin Increases the Rate and Length of Remission in Inuslin Dependent Diabetes of Recent Onset Results of a Multicentre Double-Blind Trial,"The Lancet, p. 119-124 (1986).
Fiedler, F. et al., "Purification and properties of guinea-pig submandibular-gland kallikrein," Biochem. J., 209:125-134 (1983).
Figueroa, C. D. et al., "Cellular localization of human kininogens," Agents and Actions. Supplements 38(Pt. 1):617-626 (Jan. 1992).
Fodor et al., "Multiplexed biochemical assays with biological chips," Nature, 364:555-556 (1993).
Friberg et al., "Salivary kallikrein in Sjogren's syndrome," Clinical and Experimental Rheumatology (1988) 6:135-138.
Friedman, A. et al., "Induction of anergy or active suppression following oral tolerance is determined by antigen dosage," PNAS USA, 91:6688-6692 (Jul. 1994).
Fries et al., "The dimensions of health outcomes: The health assessment questionnaire, disability and pain scales," The Journal of Rheumatology (1982) 9(5):789-793.
Fuchtenbusch, M. et al., "Delay of Type 1 diabetes in high risk, first degree relatives by parenteral antigen administration: The Schwabing Insulin Prophylaxis Pilot Trial," Diabetologica, 41:536-541 (1998).
Fuller et al., "The cellular physiology of glandular kallikrein," Kidney International (1986) 29: 953-964.
Gallop et al., "Applications of combinatorial technologies to drug discovery. 1. Background and peptide combinatorial libraries," J. Med. Chem., 37(9):1233-1251 (1994).
Garrigue-Antar et al., "Optimisation of CCL64-based bioassay for TGF-β," Journal of Immunological Methods, (1995) 186:267-274.
GenBank Accession No. AAH05313.1, Kallikrein 1 [*Homo sapiens*], Nov. 3, 2006.
GenBank Accession No. AAG11389.1, kallikrein [*Mus musculus*], Oct. 11, 2000.
GenBank Accession No. NP_113711.1, kallikrein-1 [Rattus norvegicus], Nov. 12, 2010.
Geterud et al., "Swallowing problems in rheumatoid arthritis," Acta Otolaryngol (Stockh) (1991) 111:1153-1161.
Giannoukakis, N., "Drug evaluation: BIM-51077, a dipeptidyl peptidase-IV-resistant glucagon-like peptide-1 analog," Curr. Opin. Investig. Drugs, 8(10):842-848 (2007).
Gimsa et al., "Type II collagen serology: A guide to clinical responsiveness to oral tolerance?" Rheumatol Int. (1997) 16:237-240.
Gordon et al., "Applications of combinatorial technologies to drug discovery. 2. Combinatorial organic synthesis, library screening strategies, and future directions," J. Med. Chem., 37(10):1385-1401 (1994).
Grabley, S. et al., "8 tools for drug discovery: Natural product-based libraries," Ernst Schering Research Foundation Workshop, 32:217-252 (2000).
Greaves et al., "Anionic salivary proteins associated with connective tissue disorders: sialated tissue kallikreins," Annals of the Rheumatic Diseases (1989) 48: 753-759.
Green, B. D. et al., "Novel glucagon-like peptide-1 (GLP-1) analog (Val$^8$)GLP-1 results in significant improvements of glucose tolerance and pancreatic β-Cell function after 3-week daily administration in obese diabetic (ob/ob) mice," The Journal of Pharmacology and Experimental Therapeutics, 318(2):914-921 (2006).
Griesbacher, T. et al., "Involvement of tissue kallikrein but not plasma kallikrein in the development of symptoms mediated by endogenous kinins in acute pancreatitis in rats," British J of Pharmacology, 137(5):692-700 (2002).
Griffiths et al., "Immunogenetic control of experimental Type II collagen-induced arthritis," Arthritis and Rheumatism (1981) 24(6): 781-789.
Hial, V. et al., "Purification and properties of a human urinary kallikrein (kininogenase)," Biochemistry, 13(21):4311-4318 (1974).
Harpel, P. C., "Studies on the interaction between collagen and a plasma kallikrein-like activity," J. Clin. Invest., 51:1813-1822 (1972).
Hernandez, C. C. et al., "Kininogen-kallikrein-kinin system in plasma and saliva of patients with Sjogren's syndrome," J. Rheumatol., 25:2381-2384 (1998).
Higashi et al., "Relationship Between Insulin Resistance and Endothelium-Dependent Vascular Relaxation in Patients with Essential Hypertension," Hypertension, 29:280-285 (1997).
Holz, "Giucagoi-Like Peptide-1 Synthetic Analogs: New Therapeutic Agents for Use in the Treatment of Diabetes Mellitus," Curr. Med Chem, 10(22):2471-2483 (2003).
Houghten et al., "Drug discovery and vaccine development using mixture-based synthetic combinatorial libraries," Drug Discovery Today, 5(7):276-285 (2000).
Houghten et al., "The use of synthetic peptide combinatorial libraries for the identification of bioactive peptides," Biotechniques, 13(3):412-421 (1992).
Hsu, C. C. et al., "Five cysteine-containing compounds delay diabetic deterioration in balb/cA mice," J. Nutr., 134(12):3245-3249 (2004).
Hu, Z. Q. al., "Enhancement of lymphocyte proliferation by mouse glandular kallikrein," Immunology Letters (1992) 32:85-90.
Ishizaka, K., "Twenty years with IgE: From the identification of IgE to regulatory factors for the IgE response," American Association of Immunologists Presidential Address, The Journal of Immunology (1985) 135(1): i-x.
Jaffa, A. A. et al., "Plasma Prekallikrein: A risk marker for hypertension and nephropathy in type 1 diabetes," Diabetes, 52(5):1215-1221 (2003).
James, M. N. et al., "Amino acid sequence alignment of bacterial and mammalian pancreatic serine proteases based on topological equivalences," Can. J. Biochem., 56(6):396-402 (1978).
Jensen et al., "Salivary acidic proline-rich proteins in rheumatoid arthritis," Ann NY Acad Sci. (1998) 842:209-211.
Jenzano et al., "The assay of glandular kallikrein and prekallikrein in human mixed saliva," Archs Oral Biol., (1988) 33(9):641-644.
Jong, Y.-J. et al., "Human bradykinin B2 receptors isolated by receptor-specific monoclonal antibodies are tyrosine phosphorylated," Proceedings of the National Academy of Sciences of the United States of America, 90(23):10994-10998 (1993).

(56) References Cited

OTHER PUBLICATIONS

Karaca et al., "Functional pancreatic beta-cell mass: involvement in type 2 diabetes and therapeutic intervention," Diabetes Metab., 65:77-84 (2009).
Kehrl et al., "Further studies of the role of transforming growth factor-β in human B cell function," The Journal of Immunology, (1989) 6:1868-1874.
Kehrl et al., "Transforming growth factor-β suppresses human B lymphocyte lg production by inhibiting synthesis and the switch from the membrane form to the secreted form of lg mRNA," The Journal of Immunology (1991) 146:4016-4023.
Kelly et al., "Decreased salivary epidermal growth factor in rheumatoid disease: a possible mechanism for increased susceptibility to gastric ulceration," Brit. Med. J., (1990) 301:422-423.
Kemp et al., "Suppression and enhancement of in vitro lymphocyte reactivity by factors in rat submandublar gland extracts," Immunology (1985) 56:261-267.
Kemp et al., "Inhibition of interleukin I activity by a factor in submandibular glands of rats," The Journal of Immunology (1986) 137(7):2245-2251.
Kerby et al., "Salivary kallikrein levels in normal and in rheumatoid individuals," J Lab Clin Med. (1968) 71(4):704-708.
Kim, J. K. et al., "Multiple sclerosis: An Important Role for Post-Translational Modifications of Myelin Basic Protein in Pathogenesis," Molecular and Cellular Proteomics, 2:453-462 (2003).
Kim, Y. et al., "Identification of Hnrph3 as an autoantigen for acute anterior uveitis," Clinical Immunology, 138:60-66 (2011).
Knoerzer et al., "Collagen-induced arthritis in the BB rat," J. Clin. Invest. (1995) 96:987-993.
Kolodka, T. et al., "Preclinical Characterization of Recombinant Human Tissue Kallikrein-1 as a Novel Treatment for Type 2 Diabetes Mellitus," (2014), PloS One 9(8):e103981. doi:10.1371/journal.pone.0103981, 8 pages.
Kremer, J. M., "Methotrexate and emerging therapies," Rheumatic Diseases Clinics of North America (1998) 24(3):651-658.
Lam et al., "A new type of synthetic peptide library for identifying ligand-binding activity," Nature, 354:82-84 (1991).
Lampeter, E. F. et al., "The Deutsche Nicotinamide Intervention Study: An Attempt to Prevent Type 1 Diabetes," Diabetes, 47:980-984 (1998).
Larsen et al., "Individual variations of pH, buffer capacity, and concentrations of calcium and phosphate in unstimulated whole saliva," Archives of Oral Biology (1999) 44:111-117.
Lautt, W. W. et al., "Rapid insulin sensitivity test (RIST)," Can. J. Physiol. Pharmacol., 76:1080-1086 (1998).
Lautt, W. W., "The HISS story overview: a novel hepatic neurohumoral regulation of peripheral insulin sensitivity in health and diabetes," Canadian Journal of Physiology Pharmacology, 77:553-562 (1999).
Lautt, W. W. et al., "Hepatic parasympathetic (HISS) nerve-dependent control of peripheral insulin sensitivity is determined by feeding and fasting: dynamic control of HISS-dependent insulin action," American Journal of Physiology—Gastrointestinal and Liver Physiology, 281:G29-G36 (2001).
Lautt, W., "A new paradigm for diabetes and obesity: the hepatic insulin sensitizing substance (HISS) hypothsis," J. Pharmacol. Sci., 95(1):9-17 (2004).
Laxmikanthan et al., "1.70 A X-Ray Structure of Human apo Kallikrein 1: Structural Changes Upon Peptide Inhibitor/Substrate Binding," Proteins: Structure, Function, and Bioinformatics, 58:802-814 (2005).
Leger, R. et al., "Identification of CJC-1131-albumin bioconjugate as a stable and bioactive GLP-1(7-36) analog," Bioorg. Med. Chem. Lett., 14(17):4395-4398 (2004).
Lee et al., "Co-stimulation of T cell proliferation by transforming growth factor-β1," The Journal of Immunology (1991) 147(4):1127-1133.
Lenander-Lumikari et al., "Stimulated salivary flow rate and composition in asthmatic and non-asthmatic adults," Archives of Oral Biology, 43:151-156 (1998).

Li, H. et al., "Substrate specificity of human kallikreins 1 and 6 determined by phage display," Protein Science, 17:664-672 (2008).
Li, H. et al., "Tissue kallikrein protects against pressure overload-induced cardiac hypertrophy through kinin B2 receptor and glycogen synthase kinase-3β activation," Cardiovascular Research, 73(1):130-142 (2007).
Lindsay et al., "Inhibition of dipeptidyl peptidase IV activity by oral metformin in Type 2 diabetes," Diabetic Medicine, 22:654-657 (2005).
Majewska et al., "Epicutaneous immunization with myelin basic protein protects from the experimental autoimmune encephalomyelitis," Pharmalogical Reports, (2007) 59 74-79.
Montanari, D. et al., "Kallikrein gene delivery improves serum glucose and lipid profiles and cardiac function in streptozotocin-induced diabetic rats," Diabetes, 54:1573-1580 (2005).
Manto, A. et al., "Urinary kallikrein excretion in Type 1 (insulin-dependent) diabetes mellitus," Diabetologia, 36(5):423-427 (1993).
Material Safety Data Sheet, Azo dye-impregnated collagen, Sigma-Aldrich (version 4.0), Feb. 27, 2010.
Matsushita, S. et al., "Biphasic effect of kallikrein on IgE and IgGI syntheses by LPS/IL4-stimulated B-cells," Cellular Immunology, 146:210-214 (1993).
Matthews et al., "Salivary secretion and connective tissue disease in man," Annals of the Rheumatic Diseases, (1985) 44: 20-26.
Mazzone, P et al., "Our new understanding of pulmonary alveolar proteinosis: What an internist needs to know," Cleveland Clinic Journal of Medicine, 68(12): 977-978 (2001).
McCartney-Francis et al., "Transforming growth factor β: a matter of life and death," Journal of Leukocyte Biology (1994) 55:401-409.
McCormack et al., "Molecular forms of prostate-specific antigen and the human kallikrein gene family: A new era," Urology (1995) 45(5):729-744.
McIntosh et al., "Antigen-specific suppressor macrophages induced by culture with cyclosporine A plus acetoylcholine receptor," Journal of Neuroimmunology (1989) 25:75-89.
McIntosh et al., "Tolerance to acetylcholine receptor induced by AChR-coupled syngeneic cells," Journal of Neuroimmunology (1992) 38:75-84.
Medline Plus, Type 1 Diabetes, U.S. National Library of Medicine, NIH, [online], [Retrieved on Aug. 28, 2013], [Retrieved from the Internet: URL: <http://www.nlm.nih.gov/medlineplus/ency/article/000305.htm>], 7 pages.
Meier, J. J., "Beta cell mass in diabetes: a realistic therapeutic target?," Diabetologia, 51(5):703-713 (2008).
Miranda et al., "The amidase activity of human tissue kallikrein is significantly higher in the urine of patients with either type 1 or gestational diabetes mellitus," Int. J. Diabetes & Metab., 18:124-131 (2010).
Moore, M. C. et al., "Effect of hepatic denervation on peripheral insulin sensitivity in concious dogs," American Journal of Physiology—Endocrinology and Metabolism, 282: E286-296 (2002).
Morris et al., "Hapten-induced model of chronic inflammation and ulceration in the rat colon," Gastroenterology (1989) 96:795-803.
Moser, A. et al, "Beta cell antigens in type 1 diabetes: triggers in pathogenesis and therapeutic targets," F1000 Biology Reports 2010, 2:75 (doi:10.3410/B2-75), 4 pages.
Nagy, E. et al., "Immunoregulatory effects of glandular kallikrein from the salivary submandibular gland of rats," Neuroimmunomodulation (1997) 4:107-112.
Naslund, E. et al., "Glucagon-like peptide-1 analogue LY315902: effect on intestinal motility and release of insulin and somatostatin," Regul. Pept., 106(1-3):89-95 (2002).
Nathan, D. M. et al., "Medical Management of Hyperglycemia in Type 2 Diabetes: A Consensus Algorithm for the Initiation and Adjustment of Therapy," Diabetes Care, 32(1):193-203 (2009).
Naughton, M. A. et al., "Esteropeptidase and thymotropic activity of a protein isolated from the mouse submaxillary gland," Biochimica et Biophysica Acta (1972) 263:106-114.
Norris, S. L. et al., "Drug class review: Newer drugs for the treatment of diabetes mellitus," Final Report, Aug. 2008, Oregon Health & Science University, Portland, Oregon (2008).

(56) References Cited

OTHER PUBLICATIONS

OriGene, "KLK1 (NM_002257) Human cDNA Clone," [online], [Retrieved on Feb. 18, 2012], [Retrieved from the Internet: <URL: http://www.origene.com/human_cdna/NM_002257/SC122623/KLK1.aspx>], 1 page.
Ottlecz, A. et al., "Plasmakinin system in alloxan diabetic rats," Adv. Biosci., 17:57-63 (1978).
Perris, A. D., et al., "The mitogenic action of bradykinin on thymic lymphocytes and its dependence on calcium," Proc. Soc. Exp. Biol. Med., 130:1198-1201 (1969).
Pizard, A. et al., "Genetic deficiency in tissue kallikrein activity in mouse and man: effect on arteries, heart and kidney," Biological Chemistry, 389(6):701-706 (2008).
Predki, P. et al., "Protein microarrays: A new tool for profiling antibody cross-reactivity," Human Antibodies, 14:7-15 (2005).
Proud et al., "Kinins are generated in vivo following nasal airway challenge of allergic individuals with allergen," J. Clin. Invest. (1983) 72:1678-1685.
Rader, C., "Antibody libraries in drug and target discovery," Drug Discovery Today, 6(1):36-43 (2001).
Reibman et al., "Transforming growth factor β1, a potent chemoattractant for human neutrophils, bypasses classic signal-transduction pathways," Proc. Natl. Acad. Sci. (1991) 88:6805-6809.
Richards, R. I. et al., Mouse glandular kallikrien genes, The Journal of Biological Chemistry, 257(6):2758-2761 (1982).
Roberts et al., "New class of transforming growth factors potentiated by epidermal growth factor: Isolation from non-neoplastic tissues," Proc. Natl. Acad. Sci. (1981) 78(9):5339-5343.
Roberts et al., "The transforming growth-factor-βs," Handbook of Pharmacology 95(1990):Chapter 8:419-472.
Robinson et al., "Transfer of human serum IgG to nonobese diabetic Igµnull mice reveals a role for autoantibodies in the loss of secretory function of exocrine tissues in Sjogren's syndrome," Proc. Natl. Acad. Sci. (1998) 95: 7538-7543.
Rothschild, A. M. et al., "Increased kininogen levels observed in plasma of diabetic patients are corrected by the administration of insulin," Hormone and Metabolic Research, 31(5):326-328 (1999).
Russell et al., "Investigation of xerostomia in patients with rheumatoid arthritis," JADA (1998) 129: 733-739.
Sabbadini et al., "The submandibular gland: A key organ in the neuro-immuno-regulatory network?" Neuroimmunomodulation, 2:184-202 (1995).
Sagara, T. et al., "Reduction of collagen type 1 in the ciliary muscle of inflamed monkey eyes," Investigative Ophthalmology & Visual Science, 40:2568-2576 (1999).
Salgame et al., "Differing lymphokine profiles of functional subsets of human CD4 and CD5 cell clones," Science (1991) 254 (5029): 279-282.
Sartor et al., "Selective kallikrein-kinin system activation in inbred rats differentially susceptible to granulomatous enterocolitis," Gastroenteroloy (1996) 110:1467-1481.
Scott et al., "Searching for peptide ligands with an epitope library," Science, 249 (4967):386-390 (1990).
Shaw, J. et al., "Regulation of human tissue kallikrein-related peptidase expression by steroid hormones in 32 cell lines," Biological Chemistry, 389(11):1409-1419 (2008).
Simson, J. A. V. et al., "Histopathology of lymphatic tissue in transgenic mice expressing human tissue kallikrein gene," Lab. Invest., 71(5):680-687 (1994).
Simson, J. A. V., "Localization of kallikrein gene family proteases in rat tissues," Agents and Actions-Suppl., 38(1):595 (1992).
Song et al., "The thymus plays a role in oral tolerance in experimental autoimmune encephalomyelitis," The Journal of Immunology (2006) 177:1500-1509.
Song, G. et al., "New Centromere Autoantigens Identified in Systemic Sclerosis Using Centromere Protein Microarrays," Journal of Rheumatology, 40:461-468 (2013).

Spinetti, G. et al., "Tissue kallikrein is essential for invasive capacity of circulating proangiogenic cells," Circulation Research, 108(3):284-293 (Feb. 2011), doi: 10.1161/CIRCRESAHA.110.236786. Epub Dec. 16, 2010.
Steinbrocker et al., "Therapeutic criteria in rheumatoid arthritis," The Journal of the American Medical Association (1949) 140(8):659-662.
Sun, H. et al., "Prolonged hypotensive effect of human tissue kallikrein gene delivery and recombinant enzyme administration in spontaneous hypertension rats," Experimental and Molecular Medicine, 36(1):23-27 (2004).
Swift, G. H. et al., "Rat pancreatic kallikrein mRNA: Nucleotide sequence and amino acid sequence of th encoded preproenzyme," Proc. Nat. Acad. Sci. U.S.A., 79:7263-7267 (1982).
Synopsis "Type 2 Diabetes: Insulin Resistance May Be the Result of Mitochondrial Dysfunction.," PLOS Med 2(9): e292, 2 pages (2005).
Szodoray, P. et al., "Anti-citrullinated protein/peptide autoantibodies in association with genetic and environmental factors as indicators of disease outcome in rheumatoid arthritis," Autoimmunity Reviews, 9:140-143 (2010).
Takada, K. et al., "Autoimmunity against a tissue kallikrein in IQI/Jic mice: a model for Sjogren's syndrome," J. Biol. Chem., 280:3982-3988 (2005).
Takayama et al., "Characterization of the precursor of prostate-specific antigen," The Journal of Biological Chemistry (1997) 272(34):21582-21588.
Teitelbaum et al., "Immunomodulation of experimental autoimmune encephalomyelitis by oral administration of copolymer I," Proc. Natl. Acad. Sci. USA (1999) 96: 3842-3847.
TEVA Marion, "Copaxone (glatiramer acetate injection)," [online], [Retrieved on the internet: URL: <http://www.msakc.org/Articles/Copaxone.htm>, [Retrieved on Jul. 31, 2008], 4 pages.
TEVA Pharmaceutical Industries Ltd., "Copaxone (glatiramer acetate injection)," Package Insert (May 2007), 4 pages.
Thorkildsen, C. et al., "Glucagon-like peptide 1 receptor agonist ZP10A increases insulin mRNA expression and prevents diabetic progression in db/db mice," The Journal of Pharmacology and Experimental Therapeutics, 307(2):490-496 (2003).
Tian, L. et al., "Reversal of New-Onset Diabetes through Modulating Inflammation and Stimulating β-Cell Replication in Nonobese Diabetic Mice by a Dipeptidyl Peptidase IV Inhibitor," Endocrinology, Jul. 2010, 151(7):3049-3060.
Trautschold, I., "Assay methods in the kinin system," Handbook of Experimental Pharmacoloy (1970) 25: 52-81.
Trentham, D. E., "Oral tolerization as a treatment oftheumatoid arthritis," Rheumatic Diseases Clinics of North America (1998) 24 (3): 525-536.
Tschetsche, H. et al., "The primary structure of porcine gladular kallikreins," Adv. Exp. Med. Biol., 120A:245-260 (1979).
Tschope et al., "Functional, biochemical, and molecular investigations of renal kallikrein-kinin system in diabetic rats," Am. J. Physiol. Heart Circ. Physiol., 277:H2333-H2340 (1999).
Uehara, S. et al., "Kallikrein-kinin system in diabetic patients," Drug. Res., 38(5):721-723 (1988).
Verwaerde, C. et al., "Properties of serine proteases of Schistosoma mansoni Schistosomula involved in the regulation of IgE synthesis," Scand. J. Immunol. (1988) 27:17-24.
Vojdani et al., "Methyl tertiary-butyl ether antibodies among gasoline service station attendants," Ann. NY Acad. Sci., 837:96-104 (1997) (Abstract).
Wahl et al., "Transforming growth factor type β induces monocyte chemotaxis and growth factor production," Proc. Natl. Acad. Sci. (1987) 84: 5788-5792.
Wahl, S. M., "Transforming growth factor beta (TGF-β) in inflammation: A cause and a cure," Journal of Clinical Immunology (1992) 12(2):61-74.
Wahren, J. et al., "Role of C-peptide in human physiology," Am. J. Physiol. Endocrinol. Metab., 278(5):E759-E768 (2000).
Walker et al., "Interaction of human IgG chimeric antibodies with the human FcRI and FcRII receptors: Requirements for antibody-mediated host cell-target cell interaction," Molecular Immunology, 26(4):403-411 (1989).

(56) References Cited

OTHER PUBLICATIONS

Wang et al., "Investigation of the clinical value of total saliva flow rates," Archives of Oral Biology (1998) 43:39-43.
Weinblatt et al., "Efficacy of low-dose methotrexate in rheumatoid arthritis," The New England Journal of Medicine (1985) 312(13):818-822.
Weiner, H. L., "Oral tolerance for the treatment of autoimmune diseases," Annu. Rev. Med., 48:341-351 (1997).
Weiner, H. L. et al., "Oral tolerance: immunologic mechanisms and treatment of animal and human organ-specific autoimmune diseases by oral administration of autoantigens," Annu. Rev. Immunol., 12:809-837 (1994).
Weiner, H.L., "Oral tolerance with Copolymer 1 for the treatment of multiple sclerosis," Proc. Natl. Acad. Sci. USA (1999) 96: 3333-3335.
Weiner, H. L., "Oral tolerance: immune mechanisms and treatment of autoimmune diseases," Immunol. Today, 18(7):335-343 (1997).
Weir et al., "Five Stages of Evolving β-Cell Dysfunction During Progression to Diabetes," Diabetes, 53(3):S16-S21 (2004).
Wikipedia, "Kidney" [online], [Retrieved on Jan. 31, 2005], [Retrieved from the Internet: URL: <http://www.wikipedia.org/wiki/Kidney>], 5 pages.
Wilson, R. D. et al., "Fructose-fed streptozotocin-injected rat: an alternative model for type 2 diabetes," Pharmacological Reports, v.64, pp. 129-139 (2012).
Wines, D. R. et al., "Organization and expression of the rat kallikrein gene family," J. Biol. Chem., 264(13):7653-7662 (1989).
Wolinsky, J.S., "The use of glatiramer acetate in the treatment of multiple sclerosis," Adv. Neural. (2006) 98:273-92 (Abstract).
Yamamura et al., "Defining protective responses to pathogens: Cytokine profiles in leprosy lesions," Science (1991) 254 (5029):277-279.
Yao et al., "Tissue kallikrein infusion prevents cardiomyocyte apoptosis, inflammation and ventricular remodeling after myocardial infarction," Regulatory Peptides, 140(1-2):12-20 (2007).
Yao, Y. et al., "Tissue kallikrein promotes neovascularization and improves cardic function by the Akt-glycogen synthase kinase-3β pathway," Cardiovascular Research, 80(3):354-364 (2008).
Yin et al., "Kallikrein/kinin protects against myocardial apoptosis after ischemia/reperfusion via akt-glycogen synthase kinase-3 and Akt-Bad-14-3-3 signaling pathways," The Journal of Biological Chemistry, 280(9):8022-8030 (2005).
Yki-Jarvinen, "Combination Therapies with Insulin in Type 2 Diabetes," Deabetes Care, 24(4):758-767 (2001).
Yost et al., "Tandem quadrupole mass spectrometry," In: Tandem Mass Spectrometry, McLafferty (Ed.), Wiley & Sons, New York, pp. 175-195 (1983).
Yousef, G. M. et al., "Molecular cloning of the human kallikrein 15 gene (KLK15)," J. Biol. Chem., 276(1):53-61 (2001).
Yousef, G. et al., "Genomic organization of the human kallikrein gene family on chromosome 19q13.3-q13.4," Biochemical and Biophysical Research Communications, 276(1):125-133 (2000).
Yousef, G. et al., "In-silico analysis of kallikrein gene expression in pancreatic and colon cancers," Anticancer Research, 24(1):43-51 (2004).
Yuan, G. et al., "Tissue Kallikrein Reverses Insulin Resistance and Attenuates Nephropathy in Diabetic Rats by Activation of Phosphatidylino sitol 3-Kinase/Protein Kinase B and Adenosine 5-Monophosphate-Activated Protein Kinase SiQnalinQ Pathways," Endocrinology, 148(5):2016-2026 (2007).
Zhao et al., "A coding polymorphism of the kallikrein 1 gene is associated with essential hypertension: a tagging SNP-based association study in a Chinese Han population," J. Hypertens., 25:1821-1827 (2007).
Zhao et al., "Gene therapy with human tissue kallikrein reduces hypertension and hyperinsulinemia in fructose-induced hypertensive rats," Hypertension, 42:1026-1033 (2003).
Non-Final Office Action for U.S. Appl. No. 13/909,220, dated May 15, 2014, 16 pages.
Response to Non-Final Office Action for U.S. Appl. No. 13/909,220, filed Aug. 15, 2014.
Final Office Action for U.S. Appl. No. 13/909,220, dated Oct. 3, 2014, 16 pages.
International Search Report and Written Opinion for International Application No. PCT/CA2013/050425, dated Oct. 4, 2013.
International Search Report and Written Opinion for International Application No. PCT/CA2013/050395, dated Sep. 19, 2013.
International Search Report and Written Opinion for International Application No. PCT/CA2013/050755, dated Dec. 30, 2013.
Ausubel et al., "Current Protocols in Molecular Biology," 1989; cover page, title page and table of contents only, 22 pages.
Bork et al., "Increasing the sialylation of therapeutic glycoproteins: The potential of the sialic acid biosynthetic pathway," J Pharm Sci, Oct. 2009;98(10):3499-3508.
Bothwell, M. A. et al., "The relationship between glandular kallikrein and growth factor-processing proteases of mouse submaxillary gland," The Journal of Biological Chemistry, Aug. 10, 1979;254(15):7287-7294.
Chan, H. et al., "Expression and characterization of human tissue kallikrein variants," Protein Expr. and Purifi., Apr. 1998;12(3):361-370.
Chao, J. et al., "Functional analysis of human tissue kallikrein in transgenic mouse models," Hypertension, Mar. 1996;27(3 Pt 2):491-494.
Chatzigeorgiou et al., "The Use of Animal Models in the Study of Diabetes Mellitus," In Vivo, Mar.-Apr. 2009;23(2):245-258.
Devasahayam, "Factors affecting the expression of recombinant glycoproteins," Indian J Med Research, Jul. 2007;126:22-27.
Edgerton et al., "Inhaled Insulin is Associated wth Prolonged Enhancement of Glucose Disposal in Muscle and Liver in the Canine," J Pharmacal Exp Ther., Mar. 2009; 328(3):970-975.
FDA Guidance for Industry: Estimating the Maximum Safe Starting Dose in Initial Clinical Trial for Therapeutics in Adult Healthy Volunteers, Appendix D: Converting Animal doses to human equivalent doses, Jul. 2005; 30 pgs.
Genbank Accession No. AAA39349 .1 National Center for Biotechnology Information, National Library of Medicine, National Institutes of Health, GenBank Locus AAA39349, Accession No. AAA39349, "Kallikrein 1 [*Mus musculus domesticus*]," [online]. Bethesda, MD [retrieved on Jun. 4, 2014]. Retrieved from the Internet:<URL:httn://www.ncbi.nlm.nih.gov/protein/AAA39349.1>; 2 pages.
Genbank Accession No. AAI51559.1 National Center for Biotechnology Information, National Library ofMedicine, National Institutes of Health, GenBank Locus AAI51599, Accession No. AAI51559; Version No. AAI51559.1 GI:154426202, [online]. Bethesda, MD [retrieved on Aug. 11, 2014]. Retrieved from the Internet: <URL: http://www.ncbi.nlm.nih.gov/protein/154426202>; 2 pages.
Genbank Accession No. CAE51906.1National Center for Biotechnology Information, National Library ofMedicine, National Institutes ofHealth, GenBank Locus AE51906, Accession No. AE51906, "TPA: kallikrein 1 precursor [Rattus norvegicus]," [online]. Bethesda, MD [retrieved on Jun. 4, 2014]. Retrieved from the Internet<URL: http://www /ncbi.nlm.nih. gov /protein/CAE51906.1 >; 2 pages.
Genbank Accession No. NP 002248.1 National Center for Biotechnology Information, National Library of Medicine, National Institutes of Health, GenBank Locus NP 002248, Accession No. NP 002248, "kallikrein-1 prepoprotein [*Homo sapiens*]," [online]. Bethesda, MD [retrieved on Jun. 4, 2014]. Retrieved from the Internet<URL: http://www/ncbi.nlm.nih.gov/protein/NP 002248.1>; 3 pages.
Goodman, "Toward Evidence-Based Medical Statistics.2: The Bayes Factor," Ann Intern. Med, Jun. 15, 1999;130(12):1005-1013.
Graham et al., "Characteristics of a Human Cell Line Transformed by DNA from Human Adenovirus Type 5," J. Gen Viral., Jul. 1977;36:59-72.
Jaffa et al., "Induction of renal kallikrein and renin gene expression by insulin and IGF-1 in the diabetic rat," Diabetes, 1997;46:2049-2056.

(56) References Cited

OTHER PUBLICATIONS

Kellermann, Jr. et al., "Human urinary kallikrein-amino acid sequence and carbohydrate attachment sites," Protein Seq Data Anal., Feb. 1988; 1(3):177-182.
Kroon et al., "The transcriptional regulatory strategy of the rat tissue kallikrein gene family," Genes Funct., Dec. 1997;1(5):309-319.
Lin, F-K. et al., "Molecular cloning and sequence analysis of the monkey and human tissue kallikrein genes," Biophys. Biochem. Acta, 1173:325-328 (1993).
Logan, J. et al., "Adenovirus tripartite leader sequence enhances translation of mRNAs later after infection," PNAS USA, Jun. 1984;81(12):3655-3659.
Lu, H. S. et al., "Purification and characterization of human tissue prokallikrein and kallikrein isoforms expressed in Chinese hamster ovary cells," Protein Expression and Purification, Sep. 1996;8(2):227-237.
Lu, H. S. et al., "Human urinary kallikrein: complete amino acid sequence and sites of glycosylation," Int. J Peptide Protein Res., 1989;33:237-249.
Mather, "Establishment and Characterization of Two Distinct Mouse Testicular Epithelial Cell Lines," Biol Reprod., Aug. 1, 1980;23 :243-251.
Mather et al., "Culture of Testicular Cells in Hormone-Supplemented Serum-Free Medium," Annals NY Acad Sci, Jun. 1982:383:44-68.
Mayfield, R. K. et al., "Skeletal muscle kallikrein. Potential role in metabolic regulation," Diabetes, Jan. 1996;45 Suppl 1:S20-S23.
Merrifield, "Solid Phase Peptide Synthesis. I. The Synthesis of a Tetrapeptide," J Am Chem Soc., 1963;85(14):2149-2154.
Montanari, D., "Kallikrein gene delivery improves serum glucose and lipid profiles and cardiac function in streptozotocin-induced diabetic rats," Diabetes, May 2005;54(5):1573-80.
Moreau, M. E. et al., "The kallikrein-kinin system: current and future pharmacological targets," Journal of Pharmacological Sciences, Sep. 2005;99(1):6-38.
Ole-Moi et al., "Structural studies of a human urinary kallikrein (urokallikrein)," PNAS, Jul. 1979;76(7):3121-3125.
Oza et al., "A Simple High-Yield Procedure for Isolation of Human Urinary Kallikreins," Biochem J, Apr. 1, 1978;171(1): 285-288.
Rajapakse et al., "Estrogen-dependent expression of the tissue kallikrein gene (Klk1) in the mouse uterus and its implications for endometrial tissue growth," Mol Reprod Dev, Aug. 2007;74(8):1053-1063.
Recombinant Human Kallikrein-1/ KLK1. Datasheet [online] SinoBiological Inc., 2011 [retrieved on Aug. 14, 2013]. [Retrieved from the Internet: <URL:http://web.archive.org/web/20110911225357/http://www.sinobiological.com/KLK1-Protein-g-284.html>]; 4.
Remington: The Science and practice of Pharmacy, Mack Publishing Company, Easton, PA, Edition 21; 2005; cover page, title page and table of contents only.
Sambrook et al., "Molecular Cloning, A Laboratory Manual," 2nd Edition. 1989; Cold Spring Harbor Laboratory Press, Nina Irwin; Table of Contents Only; 31 pages.
Sambrook et al., "Molecular Cloning, A Laboratory Manual," 3rd Edition. 2001; Table of Contents Only; 22 pages.
Schubert-Zsilavecz, M. et al., Insulin glargin—ein langwirksames Insulinanalogon: Bessere Blutzuckerwerte beim Diabetiker, Pharmazie in unserer Zeit, Mar. 2001;30(2):125-130.
Slim, R. et al., "Loss-of-function polymorphorism of the human kallikrein gene with reduced urinary kallikrein activity," J. Am. Soc. Nephrol., 2002; 13:968-976.
[No author listed], "The effect of intensive treatment of diabetes on the development and progression of long-term complications in insulin-dependent diabetes mellitus. The Diabetes Control and Complications Trial Research Group," N. Engl. J. Med., Sep. 30, 1993;329(14):977-986.
UniProtKB/Swiss-Prot Accession No. P06870; May 14, 2014, [Retrieved from the internet: URL: <www.uniprot.org/uniprot/P06870>], [Retrieved on May 3, 2014].
Urlaub, G. et al., "Isolation of Chinese hamster cells mutants deficient in dihydrofolate Reductase activity," Proc Natl Acad Sci U S A. Jul. 1980; 77(7): 4216-4220.
Watson, E. et al., "Comparison of N-linked oligosaccharides of recombinant human tissue kallikrein produced by Chinese hamster ovary cells on microcarrier beads and in serum-free suspension culture," Biotechnol. Prog., Jan.-Feb. 1994;10(1):39-44.
Yang, Q. et al., "Purification of human tissue prokallikrein excreted from insect cells by liquid chromatography," J Pharm Biomed Anal., Sep. 15, 2005;39(3-4):848-52.
Yousef, G. M. et al., "The new human tissue kallikrein gene family: structure, function, and association to disease," Endocrine Reviews, Apr. 2001;22(2):184-204.

* cited by examiner

```
SEQUENCE LISTING

<160> NUMBER OF SEQ ID NOS: 2

<210> SEQ ID NO 1
<211> LENGTH: 262
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: PROPEP
<222> LOCATION: (19)..(24)
<220> FEATURE:
<221> NAME/KEY: mat_peptide
<222> LOCATION: (25)..(262)

<400> SEQUENCE: 1

Met Trp Phe Leu Val Leu Cys Leu Ala Leu Ser Leu Gly Gly Thr Gly
                -20                 -15                 -10

Ala Ala Pro Pro Ile Gln Ser Arg Ile Val Gly Gly Trp Glu Cys Glu
             -5                  -1   1               5

Gln His Ser Gln Pro Trp Gln Ala Ala Leu Tyr His Phe Ser Thr Phe
     10                  15                  20

Gln Cys Gly Gly Ile Leu Val His Arg Gln Trp Val Leu Thr Ala Ala
 25                  30                  35                  40

His Cys Ile Ser Asp Asn Tyr Gln Leu Trp Leu Gly Arg His Asn Leu
                 45                  50                  55

Phe Asp Asp Glu Asn Thr Ala Gln Phe Val His Val Ser Glu Ser Phe
                 60                  65                  70

Pro His Pro Gly Phe Asn Met Ser Leu Leu Glu Asn His Thr Arg Gln
         75                  80                  85

Ala Asp Glu Asp Tyr Ser His Asp Leu Met Leu Leu Arg Leu Thr Glu
 90                  95                 100

Pro Ala Asp Thr Ile Thr Asp Ala Val Lys Val Val Glu Leu Pro Thr
105                 110                 115                 120

Glu Glu Pro Glu Val Gly Ser Thr Cys Leu Ala Ser Gly Trp Gly Ser
                125                 130                 135

Ile Glu Pro Glu Asn Phe Ser Phe Pro Asp Asp Leu Gln Cys Val Asp
             140                 145                 150

Leu Lys Ile Leu Pro Asn Asp Glu Cys Lys Lys Ala His Val Gln Lys
         155                 160                 165

Val Thr Asp Phe Met Leu Cys Val Gly His Leu Glu Gly Gly Lys Asp
170                 175                 180
```

```
Thr Cys Val Gly Asp Ser Gly Gly Pro Leu Met Cys Asp Gly Val Leu
185                 190                 195                 200

Gln Gly Val Thr Ser Trp Gly Tyr Val Pro Cys Gly Thr Pro Asn Lys
            205                 210                 215

Pro Ser Val Ala Val Arg Val Leu Ser Tyr Val Lys Trp Ile Glu Asp
            220                 225                 230

Thr Ile Ala Glu Asn Ser
            235

<210> SEQ ID NO 2
<211> LENGTH: 262
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: PROPEP
<222> LOCATION: (19)..(24)
<220> FEATURE:
<221> NAME/KEY: mat_peptide
<222> LOCATION: (25)..(262)

<400> SEQUENCE: 2

Met Trp Phe Leu Val Leu Cys Leu Ala Leu Ser Leu Gly Gly Thr Gly
                -20                 -15                 -10

Ala Ala Pro Pro Ile Gln Ser Arg Ile Val Gly Gly Trp Glu Cys Glu
            -5                  -1  1                   5

Gln His Ser Gln Pro Trp Gln Ala Ala Leu Tyr His Phe Ser Thr Phe
        10                  15                  20

Gln Cys Gly Gly Ile Leu Val His Arg Gln Trp Val Leu Thr Ala Ala
25                  30                  35                  40

His Cys Ile Ser Asp Asn Tyr Gln Leu Trp Leu Gly Arg His Asn Leu
                45                  50                  55

Phe Asp Asp Glu Asn Thr Ala Gln Phe Val His Val Ser Glu Ser Phe
                60                  65                  70

Pro His Pro Gly Phe Asn Met Ser Leu Leu Glu Asn His Thr Arg Gln
        75                  80                  85

Ala Asp Glu Asp Tyr Ser His Asp Leu Met Leu Leu Arg Leu Thr Glu
        90                  95                  100

Pro Ala Asp Thr Ile Thr Asp Ala Val Lys Val Val Glu Leu Pro Thr
105                 110                 115                 120

Gln Glu Pro Glu Val Gly Ser Thr Cys Leu Ala Ser Gly Trp Gly Ser
            125                 130                 135

Ile Glu Pro Glu Asn Phe Ser Phe Pro Asp Asp Leu Gln Cys Val Asp
            140                 145                 150

Leu Lys Ile Leu Pro Asn Asp Glu Cys Lys Lys Val His Val Gln Lys
            155                 160                 165

Val Thr Asp Phe Met Leu Cys Val Gly His Leu Glu Gly Gly Lys Asp
            170                 175                 180

Thr Cys Val Gly Asp Ser Gly Gly Pro Leu Met Cys Asp Gly Val Leu
185                 190                 195                 200

Gln Gly Val Thr Ser Trp Gly Tyr Val Pro Cys Gly Thr Pro Asn Lys
            205                 210                 215
```

-continued

```
Pro Ser Val Ala Val Arg Val Leu Ser Tyr Val Lys Trp Ile Glu Asp
        220                 225                 230

Thr Ile Ala Glu Asn Ser
        235
```

HUMAN TISSUE KALLIKREIN 1 GLYCOSYLATION ISOFORMS

CONTINUING APPLICATION DATA

This application claims the benefit of U.S. Provisional Application Ser. No. 61/655,388, filed Jun. 4, 2012, and U.S. Provisional Application Ser. No. 61/789,978, filed Mar. 15, 2013, each of which is incorporated by reference herein.

BACKGROUND

In healthy individuals, insulin release by the pancreas is strictly coupled to the blood glucose concentration. Elevated blood glucose levels like those occurring after meals are rapidly compensated by a corresponding rise in insulin secretion. Diabetes mellitus, or simply diabetes, is a group of metabolic diseases in which a person has high blood sugar, either because the pancreas does not produce enough insulin, or because cells do not respond to the insulin that is produced. Around 366 million people worldwide suffer from diabetes mellitus. Untreated, diabetes can cause many complications. Acute complications include diabetic ketoacidosis and nonketotic hyperosmolar coma. Serious long-term complications include cardiovascular disease, chronic renal failure, diabetic retinopathy, and diabetic neuropathy. The adequate treatment of diabetes is thus important and there is a need for improved therapies for the treatment of diabetes.

BRIEF SUMMARY OF THE INVENTION

The present invention includes a composition, comprising a first tissue kallikrein-1 (KLK1) polypeptide and a second tissue kallikrein-1 (KLK1) polypeptide:
wherein the first KLK1 polypeptide has three glycans attached at three different positions per polypeptide and the second KLK1 polypeptide has two glycans attached at two different positions per polypeptide; and
wherein the first KLK1 polypeptide and the second KLK1 polypeptides are present in the composition in a ratio ranging from about 45:55 to about 55:45.

In some aspects of a composition of the present invention, one or more of said glycans are N-linked glycans. In some aspects, one or more of the glycans are attached at amino acid residues 78, 84, or 141 of KLK1 as defined by SEQ ID NO:1. In some aspects, the three glycans of the first KLK1 polypeptide are N-linked glycans at residues 78, 84, and 141. In some aspects, the two glycans of the second KLK1 polypeptide are N-linked glycans at residues 78 and 84 but not 141. In some aspects, the ratio of first KLK1 polypeptide and the second KLK1 polypeptide in the composition is about 50:50.

The present invention includes a composition including a triple glycosylated isoform of a tissue kallikrein-1 (KLK1) polypeptide and a double glycosylated isoform of a tissue kallikrein-1 (KLK1) polypeptide, wherein the triple glycosylated isoform of the KLK1 polypeptide and the double glycosylated isoform of the KLK1 polypeptide are present in the composition in a ratio ranging from about 45:55 to about 55:45. In some aspects of a composition of the present invention, the triple glycosylated isoform includes N-linked glycans at amino acid residues 78, 84, and 141 of KLK1, as defined by SEQ ID NO:1. In some aspects, the double glycosylated isoform includes N-linked glycans at amino acid residues 78 and 84, but not at amino acid residue 141 of KLK1, as defined by SEQ ID NO:1. In some aspects, the triple glycosylated isoform and the double glycosylated isoform of KLK1 are present in the composition in a ratio of about 50:50. In some aspects of a composition of the present invention, one or more KLK1 polypeptide(s) is a human tissue kallikrein-1 (hKLK1) polypeptide.

In some aspects of a composition of the present invention, one or more KLK1 polypeptide(s) includes amino acid residues 78-141 of SEQ ID NO:1 or amino acids residues 78-141 SEQ ID NO:2.

In some aspects of a composition of the present invention, one or more KLK1 polypeptide(s) includes amino acid residues 25-262 of SEQ ID NO:1 or amino acid residues 25-262 of SEQ ID NO:2.

In some aspects of a composition of the present invention, one or more KLK1 polypeptide(s) includes an amino acid sequence having at least about 95% sequence identity to SEQ ID NO: 1 or SEQ ID NO:2.

In some aspects of a composition of the present invention, one or more KLK1 polypeptide(s) includes an amino acid sequence having at least about 95% sequence identity to amino acid residues 25-262 of SEQ ID NO:1 or SEQ ID NO:2.

In some aspects of a composition of the present invention, one or more KLK1 polypeptide(s) includes an amino acid sequence having at least about 95% sequence identity to amino acid residues 25-262 of SEQ ID NO:2, and wherein said KLK1 polypeptide(s) comprises E145 and/or A188.

In some aspects of a composition of the present invention, one or more KLK1 polypeptide(s) includes an amino acid sequence having at least about 95% sequence identity to amino acid residues 25-262 of SEQ ID NO:2, and said KLK1 polypeptide(s) comprises Q145 and/or V188.

In some aspects of a composition of the present invention, the KLK1 polypeptide(s) has SEQ ID NO:1 or SEQ ID NO:2.

In some aspects of a composition of the present invention, the KLK1 polypeptide(s) has residues 25-262 of SEQ ID NO:1 or SEQ ID NO:2.

In some aspects of a composition of the present invention, a composition further includes a pharmaceutically acceptable diluent, adjuvant, or carrier.

In some aspects of a composition of the present invention, the composition is substantially free of other glycosylated isoforms (glycoforms) of KLK1.

In some aspects of a composition of the present invention, the composition has endotoxin levels of less than about 1 EU/mg protein, host cell protein of less than about 100 ng/mg total protein, host cell DNA of less than about 10 pg/mg total protein, and/or is substantially free of aggregates (greater than about 95% appearing as a single peak by SEC HPLC).

The present invention also includes a device including a composition as described herein, wherein the device is suitable for delivering the composition subcutaneously. In some aspects, the device is a syringe. In some aspects, the syringe further includes a hypodermic needle assembly attached to the syringe. In some aspects, the syringe further includes a protective cover around the needle assembly. In some aspects, the syringe has a needle that is about ½ inch to about ⅝ of an inch in length and has a gauge of about 25 to about 31.

The present invention includes methods of treating a subject in need thereof, including administering to the subject a composition as described herein.

In some aspects of the methods of the present invention, administration is subcutaneous administration.

In some aspects of the methods of the present invention, wherein the subject has established type 1 diabetes (T1D) or type 2 diabetes (T2D). In some aspects, the subject has type 2 diabetes (T2D), insulin resistance, pre-diabetes, diabetes, impaired glucose tolerance, impaired glucose metabolism, hyperglycemia, hyperinsulinaemia, or syndrome X. In some aspects, the subject has latent autoimmune diabetes of adults (LADA).

In some aspects of the methods of the present invention, the subject is also treated with a diabetes drug. In some aspects, the diabetes drug is insulin or an incretin mimetic.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

DETAILED DESCRIPTION OF THE INVENTION

Figure 1:
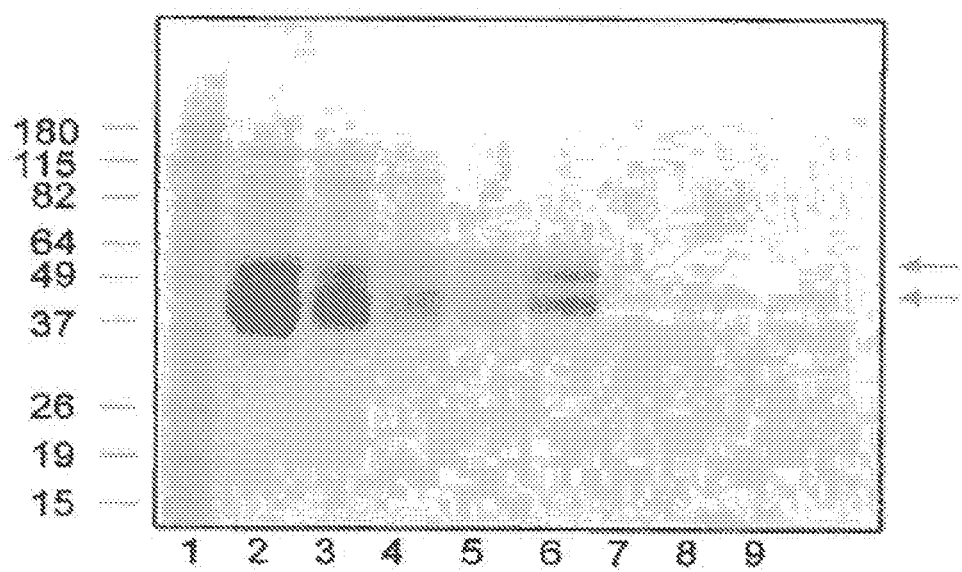
FIG. 1 is an SDS-PAGE gel stained with Coomassie Blue stain of various amounts of recombinant human KLK1 purified from CHO or 293 cell lines following transient transaction. Lane 1 is a pre-stained protein ladder, the molecular weights of the standards are written on the side (in kDa). Lanes 2-5 have KLK1 purified from CHO cells (lane 2—14 µg protein; lane 3—7 µg protein; lane 4—3.5 µg protein; lane 5—1.35 µg protein). Lane 6 has 14 µl of KLK1 protein purified from transient transfection of 293 cells.

The present invention provides compositions of tissue kallikrein-1 (KLK1) polypeptide glycoforms of defined ratios of double and triple glycosylated KLK1 polypeptides for use in the treatment of diabetes. Surprisingly, these compositions are more effective in the treatment and control of diabetes than naturally occurring compositions of KLK1.

Tissue kallikreins are members of a gene super family of serine proteases comprising at least 15 separate and distinct proteins (named tissue kallikrein 1 through 15) (Yousef et al., 2001, *Endocrine Rev;* 22:184-204). Tissue kallikrein-1 is produced predominantly in the pancreas, hence the origin of the name from the Greek term 'kallikrein.' It is also produced in the salivary glands and kidneys and is found in the urogenital tract and in skeletal muscle. Tissue kallikrein-1 is also known as KLK1, pancreatic/renal kallikrein, glandular kallikrein 1, kallikrein serine protease 1, kallikrein 1, renal kallikrein, renal/pancreas/salivary kallikrein, kidney/pancreas/salivary gland kallikrein. As used herein, the term "tissue kallikrein-1" and "KLK1" are synonymous.

Tissue kallikrein-1 is a trypsin-like serine protease. In humans and animal tissues, tissue kallikrein-1 cleaves kininogen into lysyl-bradykinin (also known as kallidin), a decapeptide kinin having physiologic effects similar to those of bradykinin. Bradykinin is a peptide that causes blood vessels to dilate and therefore causes blood pressure to lower. Kallidin is identical to bradykinin with an additional lysine residue added at the N-terminal end and signals through the bradykinin receptor.

The KLK1 gene encodes a single pre-pro-enzyme that is 262 amino acid residues in length and that includes the "pre-" sequence (residues 1-18) and the "pro-" sequence (residues 19-24), which is activated by trypsin-like enzymes. The mature and active form human KLK1 is a glycoprotein of 238 amino acid residues (residues 25-262) with a molecular weight of 26 kDa and a theoretical pI of 4.6. KLK1 has five disulphide bonds in its tertiary structure that are believed to be responsible for the protein's high stability, both against trypsin digestion and heat inactivation.

The amino acid sequence of tissue kallikrein-1 is available for a wide variety of species, including, but not limited to, human (SEQ ID NO:1 and SEQ ID NO:2), mouse (see, for example, GenBank: AAA39349.1, Feb. 1, 1994); domestic cat (see, for example, NCBI Reference Sequence: XP_003997527.1, Nov. 6, 2012); gorilla (see, for example, NCBI Reference Sequence: XP_004061305.1, Dec. 3, 2012); cattle (see, for example, GenBank: AAI51559.1, Aug. 2, 2007); dog (see, for example, CBI Reference Sequence: NP_001003262.1, Feb. 22, 2013); rat (see, for example, GenBank: CAE51906.1, Apr. 25, 2006); and olive baboon (see, for example, NCBI Reference Sequence: XP_003916022.1, Sep. 4, 2012). KLK1 is functionally conserved across species in its capacity to release the vasoactive peptide, Lys-bradykinin, from low molecular weight kininogen. A tissue kallikrein-1 polypeptide of the present invention may have any of the known amino acid sequences for KLK1, or a fragment or variant thereof.

In some aspects, a tissue kallikrein-1 polypeptide is a human tissue kallikrein-1 (hKLK1), including, but not limited to, a hKLK1 polypeptide represented by SEQ ID NO:1 or SEQ ID NO:2.

For example, hKLK1 may be represented by the amino acid sequence of GenBank Ref. NP_002248.1, having the complete KLK1 preproprotein amino acid sequence shown below:

```
                                      (SEQ ID NO: 1)
MWFLVLCLALSLGGTGAAPPIQSRIVGGWECEQHSQPWQAALYHFS    50
TFQC

GGILVHRQWLTAAHCISDNYQLWLGRHNLFDDENTAQFVHVSESFPH   100
PG

FNMSLLENHTRQADEDYSHDLMLLRLTEPADTITDAVKVVELPTEE    150
PEVG

STCLASGWGSIEPENFSFPDDLQCVDLKILPNDECKKAHVQKVTDF    200
MLCV

GHLEGGKDTCVGDSGGPLMCDGVLQGVTSWGYVPCGTPNKPSVAVR    250
VLSYVKWIEDTIAENS
```

Amino acids 1 to 18 of SEQ ID NO:1 represent the signal peptide, amino acids 19 to 24 represent propeptide sequences, and amino acids 25 to 262 represent the mature peptide. Thus, the preprotrien includes a presumptive 17-amino acid signal peptide, a 7-amino acid proenzyme fragment and a 238-amino acid mature KLK1 protein.

As described in Example 1, a second amino acid sequence for human KLK1 is represented by SEQ ID NO:2, shown below:

```
                                      (SEQ ID NO: 2)
MWFLVLCLALSLGGTGAAPPIQSRIVGGWECEQHSQPWQAALYHFS    50
TFQC

GGILVHRQWLTAAHCISDNYQLWLGRHNLFDDENTAQFVHVSESFPH   100
PG

FNMSLLENHTRQADEDYSHDLMLLRLTEPADTITDAVKVVELPTQE    150
PEVG
```
-continued
```
STCLASGWGSIEPENFSFPDDLQCVDLKILPNDECKKVHVQKVTDF    200
MLCV

GHLEGGKDTCVGDSGGPLMCDGVLQGVTSWGYVPCGTPNKPSVAVR    250
VLSYVKWIEDTIAENS
```

Again, amino acids 1 to 18 of SEQ ID NO:1 represent the signal peptide, amino acids 19 to 24 represent propeptide sequences, and amino acids 25 to 262 represent the mature peptide. Thus, the preprotrien includes a presumptive 17-amino acid signal peptide, a 7-amino acid proenzyme fragment and a 238-amino acid mature KLK1 protein.

A comparison between SEQ ID NO:1 and SEQ ID NO:2 shows two amino acid differences between the two hKLK1 amino acid sequences. Single-nucleotide polymorphism (SNP's) between the two individuals within a species account for an E to Q substitution at amino acid residue 145 of 262 and an A to V substitution at position 188 of 262. SEQ ID NO:1 has an E (glutamic acid) at position 145 and an A (alanine) at position 188, while SEQ ID NO:2 has a Q (glutamine) at position 145 and a V (valine) at position 188.

A KLK1 polypeptide of the present invention may have an E at position 145; may have a Q at position 145; may have an A at position 188; may have an A at position 188; may have an E at position 145 and an A at position 188; may have a Q at position 145 and a V at position 188; may have an Q at position 145 and an A at position 188; or may have an E at position 145 and a V at position 188.

In certain embodiments, a tissue kallikrein-1 polypeptide may include residues 1-262, residues 19-262, or residues 25-262 of a kallikrein preproprotein sequence, including, but not limited to human KLK1 having SEQ ID NO:1 or SEQ ID NO:2, and fragments and variants thereof. Fragments and variants of a KLK1 polypeptide retain the enzymatic capacity to release the vasoactive peptide, Lys-bradykinin, from low molecular weight kininogen. In some embodiments, an active variant or fragment retains serine protease activity of a KLK1 polypeptide that releases kallidin from a higher molecular weight precursor such as kininogen, or that cleaves a substrate similar to kininogen such as D-val-leu-arg-7 amido-4-trifluoromethylcoumarin to release a colorimetric or fluorometric fragment.

A "variant" of a starting or reference polypeptide is a polypeptide that has an amino acid sequence different from that of the starting or reference polypeptide. Such variants include, for example, deletions from, insertions into, and/or substitutions of residues within the amino acid sequence of the polypeptide of interest. A variant amino acid, in this context, refers to an amino acid different from the amino acid at the corresponding position in a starting or reference polypeptide sequence. Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A polypeptide variant may have at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity with a reference sequence, such as, for example, an amino acid sequence described herein.

In some aspects, a KLK1 polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to SEQ ID NO: 1, or to a fragment of SEQ ID NO:1, such as for example, residues 25-262 or residues 78-141 of SEQ ID NO:1. Such a KLK1 polypeptide may have an E or a Q at amino acid residue 145, and/or an A or a V at position 188.

In some aspects, a KLK1 polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to SEQ ID NO:2, or to a fragment of SEQ ID NO:2, such as for example, residues 25-262 or residues 78-141 of SEQ ID NO:2. Such a KLK1 polypeptide may have an E or a Q at amino acid residue 145, and/or an A or a V at position 188.

"Percent (%) amino acid sequence identity" with respect to a polypeptide is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full length of the sequences being compared. The ALIGN-2 program is publicly available through Genentech, Inc., South San Francisco, Calif.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as follows:

100 times the fraction $X/Y$, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Variants may also include sequences added to the reference polypeptide to facilitate purification, to improve metabolic half-life or to make the polypeptide easier to identify, for example, an Fc region, a His-tag, and/or a PEGylation sequence.

The term "fragment" includes smaller portions of a KLK1 polypeptide that retain the activity of a KLK1 polypeptide. Fragments includes, for example, a KLK1 polypeptide fragment that ranges in size from about 20 to about 50, about 20 to about 100, about 20 to about 150, about 20 to about 200, or about 20 to about 250 amino acids in length. In other embodiments, a KLK1 polypeptide fragment ranges in size from about 50 to about 100, about 50 to about 150, about 50 to about 200, or about 50 to about 250 amino acids in length. In other embodiments, a KLK1 polypeptide fragment ranges in size from about 100 to about 150, about 100 to about 200, about 100 to about 250, about 150 to about 175, about 150 to about 200, or about 150 to about 250 amino acids in length. In other illustrative embodiments, a KLK1 polypeptide fragment ranges in size from about 200 to about 250 amino acids in length. Certain embodiments comprise a polypeptide fragment of a full-length KLK1 of about, up to about, or at least about 50, 60, 70, 80, 90, 100, 110, 120, 130, 140, 150, 160, 170, 180, 190, 200, 210, 220, 230, 240, 250 or more (e.g., contiguous) amino acid residues. In some embodiments, a fragment may have residues 25-262 or residues 78-141 of a preproprotein sequence. In some embodiments, a fragment may be any such fragment size, as described above, of SEQ D NO: 1 or SEQ ID NO:2.

A "wild type" or "reference" sequence or the sequence of a "wild type" or "reference" protein/polypeptide may be the reference sequence from which variant polypeptides are derived through the introduction of changes. In general, the "wild type" amino acid sequence for a given protein is the sequence that is most common in nature. Similarly, a "wild type" gene sequence is the polynucleotide sequence for that gene which is most commonly found in nature. Mutations may be introduced into a "wild type" gene (and thus the protein it encodes) either through natural processes or through human induced means.

The KLK1 polypeptides and mixtures described herein may be prepared by any suitable procedure known to those of skill in the art, including recombinant techniques. As one general example, KLK1 may be prepared by a procedure including one or more of the steps of: preparing a construct comprising a polynucleotide sequence that encodes a rhKLK1 and that is operably linked to a regulatory element; introducing the construct into a host cell; culturing the host cell to express the rhKLK1; and isolating the rhKLK1 from the host cell. The construct and expression system may be such that the mature or active rhKLK1 is expressed from the host cell. Alternatively, the rhKLK1 may be expressed in an inactive form, such as a propeptide, and the rhKLK1 serine protease activity may be activated (for example, by removing the "pro" sequence) after the rhKLK1 is isolated form the host cell.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (2001), and Ausubel et al., Current Protocols in Molecular Biology (2003).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell systems. If a non-mammalian cell expression system is used (such as bacteria) then a process would need to be used to add glycan groups to the rhKLK1, such as genetically engineered cells that express the enzymes required for mammalian style glycosylation.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan and Shenk, 1984, *PNAS USA;* 81:3655-3659). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al, 1977, *J Gen Virol;* 36:59); baby hamster kidney cells (BHK, ATCC CCL 10); mouse sertoli cells (TM4, Mather, 1980, *Biol Reprod;* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., 1982, *Annals NY Acad Sci;* 383:44-68); MRC 5 cells; FS4 cells; and a human hepatoma line (Hep G2). Other useful mammalian host cell lines include Chinese hamster ovary (CHO) cells, including DHFR-CHO cells (Urlaub et al., 1980, *PNAS USA;* 77:4216)); and myeloma cell lines such as NSO and Sp2/0.

Exogenous DNA of the present invention obtained by genomic or cDNA cloning or by gene synthesis yields recombinant KLK1 (rKLK1) polypeptides. KLK1 polypeptide products of cell culture expression in vertebrate (e.g., mammalian and avian) cells may be further characterized by freedom from association with human proteins or other contaminants, which may be associated with KLK1 in its natural mammalian cellular environment or in extracellular fluids such as plasma or urine. Polypeptides of the invention may also include an initial methionine amino acid residue (at position-1). Certain embodiments therefore include host cells (e.g., eukaryotic host cells such as CHO cells, 293 cells) that comprise a recombinant or introduced polynucleotide that encodes a KLK1 polypeptide described herein, such as the polypeptide of SEQ ID NO:1 or SEQ ID NO:2. Also included are host cells that comprise a polynucleotide that encodes recombinant (e.g., non-naturally occurring) KLK-1 polypeptide described herein, such as the polypeptide of SEQ ID NO:1 or SEQ ID NO:2.

The cell culture expressed KLK1 polypeptides of the present invention may be isolated and purified by using, e.g., chromatographic separations or immunological separations involving monoclonal and/or polyclonal antibody preparations, or using inhibitors or substrates of serine proteases for affinity chromatography. As will be evident to those skilled in the art, the amino acid sequences of SEQ ID NO:1 and SEQ ID NO:2 list the sequence for pre-pro KLK1. If the gene coding for either of these sequences is expressed in mammalian cells, the 17-amino acid signal peptide (residues 1-18) should result in the KLK1 polypeptide to be secreted by the cell, and the signal peptide removed by the cell. If it is desired to not have the polypeptide secreted, or if non-mammalian cells are used for expression, a gene encoding KLK1 may be generated in which the signal sequence is omitted or replaced with another sequence. The 7 amino acid pro-sequence (residues 19-24) will inhibit the serine protease activity of the KLK1 and may be removed to allow activity of the mature KLK1 polypeptide. The pro-sequence may be removed after the KLK1 polypeptide is isolated, for example by exposing the pro-KLK1 to trypsin under conditions that will allow cleavage of the pro-sequence, or by generating a gene encoding KLK1 in which the pro-sequence omitted or replaced with another sequence.

In certain aspects, KLK1 polypeptides described herein may be "labeled" by covalent association with a detectable marker substance (such as, for example, radiolabels such as $I^{125}$ or $P^{32}$ and nonisotopic labels such as biotin) to provide reagents useful in detection and quantification of KLK1 in solid tissue and fluid samples such as blood or urine.

In addition to recombinant production methods, rhKLK1 polypeptides may be produced by direct peptide synthesis using solid-phase techniques (see, for example, Merrifield, 1963, *J Am Chem Soc;* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired polypeptide. Also included is cell-free expression of proteins. These and related embodiments typically utilize purified RNA polymerase, ribosomes, tRNA and ribonucleotides; these reagents may be produced by extraction from cells or from a cell-based expression system.

For synthesis processes that do not result in glycosylated KLK1 polypeptides, a process may also be employed to add mammalian style, N-linked glycan groups at position 78 and 84 to generate the (double glycosylated) and at position 78, 84 and 141 to generate the high-(triple glycosylated) molecular weight glycoforms of the rhKLK1 polypeptide.

Glycoforms

The present invention relates to compositions of various tissue kallikrein-1 (KLK1) polypeptide glycoforms, including compositions that comprise defined ratios of double and triple glycosylated KLK1 polypeptides and related methods of use.

The amino acid sequence of tissue kallikrein-1 indicates that there are three potential Asn-linked (N-linked) glycosylation sites on the polypeptide, at amino acid positions 78, 4, and 141 (relative to the intact preproprotein amino acid sequence shown, for example, in SEQ ID NO:1), as well as putative O-linked glycosylation sites.

KLK1 is present in circulation only in small quantities, found in the scrum at 3.5+/−0.4 ng/mL (Chao and Chao, 1996, *Hypertension;* 27:491-494). A major route of elimination of KLK1 from the human body is through the kidneys. Tissue kallikrein-1 isolated from human urine appears on a SDS PAGE gel as two bands, a low-molecular weight glycoform and a high-molecular weight glycoform. Human urinary kallikrein (HU KLK) contains approximately 30% carbohydrate content based on the molecular weight estimated by sodium dodecyl sulphate (SDS) polyacrylamide gel electrophoresis. Human kallikrein has three potential Asn-linked (N-linked) glycosylation sites at position 78, 84, and 141. On closer analysis, it has been determined that human urinary KLK1 is completely glycosylated at positions 78 and 84, but is only partially glycosylated at position 144, with only 60% glycosylation at position 141 (see WO/1989/000192). O-linked glycosylation is not detected in naturally occurring KLK1.

Analysis of recombinant human KLK1 (rhKLK1) expressed from CHO cells, detects a similar glycosylation pattern as in urine sourced human KLK1, that is, 40% of the polypeptides demonstrated N-linked glycosylation at only two positions, positions 78 and 84, and 60% of the polypeptides demonstrated N-linked glycosylation at all three positions, positions 78, 84, and 141 (Lu et al., 1996, *Protein Expression and Purification;* 8:227-237).

Prior to the present invention, the only known ratio for the low-molecular weight glycoform KLK1 to high-molecular weight glycoforms of rhKLK1 is 40:60 (low:high). As used herein, the term "glycoform" refers to various isoforms of KLK1 that differ with respect to the number or type of attached glycan groups (i.e., carbohydrates, polysaccharides, oligosaccharides, or glycosylation groups).

By SDS-PAGE analysis, KLK1 polypeptides glycosylated at only two of three available positions (positions 78 and 84) are detected as a low molecular weight band and are referred to herein as the low-molecular weight, double glycosylated glycoform of KLK1 (or as "low" or "double" KLK1). By SDS-PAGE analysis, KLK1 polypeptides glycosylated at all three positions (positions 78, 84, and 141) are detected as the high molecular weight band and are referred to herein as the high-molecular weight, triple glycosylated glycoform of KLK1 (or "high" or "triple" KLK1).

The present invention includes compositions of a first tissue kallikrein-1 polypeptide and a second tissue kallikrein-1 polypeptide, wherein the first tissue kallikrein-1 polypeptide has three glycans attached at the three different positions available for glycosylation in the polypeptide and the second tissue kallikrein-1 polypeptide has two glycans attached at only two of the three different positions available for glycosylation in the polypeptide, and wherein the first and second rhKLK1 polypeptides are present in a ratio ranging from about 45:55 to about 55:45 (high:low). In some embodiments, a ratio of high molecular weight glycoforms to low molecular weight glycoforms is about 50:50. In some embodiments, the ratio is not about 60:40 (high:low). In some embodiments, the ratio is not about 40:60 (high:low).

Isolation of Low- and High-Molecular-Weight KLK1

The ratios of the double and triple glycosylated isoforms of KLK1 may be detected and quantitated by a variety of methods, including high performance liquid chromatography (HPLC), which may include reversed phase (RP-HPLC), lectin affinity chromatography and lectin affinity electrophoresis.

In certain embodiments of the present invention, the ratio of low-(double glycosylated) and high-(triple glycosylated) molecular weight glycoforms of KLK1 is about 50:50 (low:high). In other embodiments, the ratio is between about 45:55 and about 55:45 including, for example, about 46:54, about 47:53, about 48:52, about 49:51, about 51:49, about 52:48, about 53:47, and about 54:46, including all integers and decimal points in between.

Embodiments of the present invention include compositions that comprise a recombinant KLK1 (rKLK1) polypeptide, and those that comprise a nucleic acid encoding a rKLK1 polypeptide, and mixtures of such rKLK1 polypeptide glycoforms. In particular embodiments, the KLK1 polypeptide is a recombinant human polypeptide. Recombinant human KLK1 (rhKLK1) can provide certain advantages over other sources of KLK1, such as urinary KLK1 (e.g., human KLK1 isolated from human urine), including a homogenous preparation of rhKLK1, simpler regulatory path to licensure, and options to alter the amino acid sequence or glycosylation pattern based on cell culture conditions.

As described above, recombinant human KLK1 is may be expressed as a pro-KLK1 wherein the KLK1 is attached to the pro-peptide. The pro-peptide may be removed prior to separation of the low- and high-molecular weight glycoforms, or the low- and high-molecular weight glycoforms of pro-KLK1 may be separated, and then digested to release the pro-peptide and thus generate the active KLK1. Pro-KLK1 may be activated by trypsin digestion, or other enzymes. Alternatively, a variant of KLK1 may be expressed that does not encode the pro-sequence, or encodes a pro-sequence that is cleaved by enzymes in the cell, thus generating an active KLK1.

A variety of other methods may be employed to generate mixtures of low- and high-molecular weight glycoforms of KLK1. In one embodiment, a vector encoding KLK1 may be introduced into a cell line, and a variety of clones expressing recombinant KLK1 may be screened to determine the ratio of low- and high-molecular weight glycoforms of KLK1 that are expressed. A cell line that expresses the desired ratio of low- and high-molecular weight glycoforms of KLK1 may then be chosen.

In another embodiment, a cell line may not express the desired ratio of low and high molecular weight glycoforms of KLK1, but the cell culture conditions may be manipulated until the cell line expresses low- and high-molecular weight glycoforms of KLK1 at desired ratio. Several techniques are known in the art to manipulate cell culture conditions such that the glycosylation of proteins is altered, such as the addition of certain sugars or other nutrients, levels of dissolved oxygen, etc. One exemplary article for manipulating cell culture conditions to affect changes in glycosylation is described by Devasahayam, 2007, *Indian J Med Res;* 126: 22-27.

In certain aspects, purified kallikrein or prokallikrein preparation may be separated into two different glycoforms by benzamidine—Sepharose chromatography. The benzamidine-coupled affinity column exhibits differential binding affinity to the two glycoforms. High-molecular-weight kallikrein is loosely bound to the affinity column and can be eluted with an isocratic elution using 50 mM NaCl in the elution buffer, while low-molecular-weight kallikrein binds more tightly to the benzamidine column and may be eluted by 2 M GdnHCl in 10 mM Tris-HCl buffer at pH 7.6. In another embodiment, benzamidine—Sepharose separation of high- and low-molecular-weight kallikreins may be performed using partially purified kallikrein preparation. The steps described above for purification of recombinant kallikrein may be followed to isolate a specific ratio of KLK1 glycoforms. For example, if a 50:50 (or other) mixture of low- and high-molecular weight glycoforms of KLK1 is desired, but a cell line is producing a 60:40 (high:low) mixture, the column wash conditions may be altered such that some of the high molecular weight KLK1 is eluted and not retained prior to elution of the remaining KLK1, resulting in a 50:50 mixture of glycoforms following column purification. Alternatively, the elution conditions may be manipulated such that a fraction of the high molecular weight KLK1 is retained on the column, resulting in a 50:50 mixture of glycoforms following column purification.

Hydrophobic interaction chromatography using an octyl Sepharose column may also be used to isolate high- and low-molecular-weight prokallikreins. At 1.0 M ammonium sulfate concentration, octyl Sepharose can selectively bind prokallikrein obtained from a partially purified prokallikrein preparation. Under such conditions, the unbound, residual kallikrein in the preparation elutes in the column flow-through fraction. High-molecular-weight prokallikrein in the preparation displays a weaker binding to the hydrophobic interaction column and is eluted by an isocratic elution using 1 M ammonium sulfate. Low-molecular-weight prokallikrein which exhibits a stronger binding to the column may be subsequently eluted by a reverse linear gradient from 1.0 to 0 M ammonium sulfate. As described above, if 50:50 or similar mixture of low- and high-molecular weight glycoforms of KLK1 is desired, but a cell line is producing a 60:40 (high:low) mixture, the column wash conditions may be altered such that some of the high molecular weight KLK1 is eluted and not retained prior to elution of the remaining KLK1, resulting in a 45:55 to 55:45 mixture of glycoforms following column purification. Alternatively, the elution conditions may be manipulated such that a fraction of the high molecular weight KLK1 is retained on the column, resulting in a 45:55 to 55:45 mixture of glycoforms following column purification.

In certain embodiments, the glycoforms may be isolated by reverse phase HPLC. In another embodiment, the glycoforms may be isolated by size exclusion chromatography may be employed, and preferably this separation may be employed on solutions wherein the KLK1 is either partially or substantially purified from the cell medium. Additionally, the glycoforms are separated under non-reducing or non-denaturing conditions to allow the KLK1 to maintain the internal disulfide bonds. Another technique that could be employed is separation based on charge or hydrophobicity. The third glycosylated group that distinguished the low- and high molecular weight glycoforms of KLK1 would result in the higher molecular weight glycoform being more hydrophilic. Also, the two glycoforms would differ in isoelectric point due to additional sialic acid on the carbohydrate moiety. Once separated, the glycoforms can be recombined to generate the desired ratio. Alternatively, either the low- or high-molecular weight glycoform of KLK1 may be added to a pre-existing mixture of KLK1 glycoforms until the desired ratio is achieved.

For example, to generate a 55:45 ratio from an initial mixture of 70:30 (high- to low-molecular weight glycoforms, an amount of low molecular weight KLK1 glycoform may be added until the mixture reaches 55:45. Similarly, to generate a 45:55 ratio from an initial mixture of 25:75 (high- to low-molecular weight glycoforms), additional high molecular weight KLK1 may be added to achieve a 45:55 ratio.

Purity.

Determinations of the purity of a composition of the present invention may include, but are not limited to, determination so endotoxin, host cell protein, host cell DNA, and/or percentage single peak purity by SEC HPLC.

Determination of Host Cell Protein.

Purity may be characterized in relation to the levels of host cell proteins. The host cells used for recombinant expression may range from bacteria and yeast to cell lines derived from mammalian or insect species. The cells contain hundreds to thousands of host cell proteins (HCPs) and other biomolecules that could contaminate the final product. The HCP may be secreted along with the protein of interest, or released by accidental lysing of the cells, and may contaminate the protein of interest. Two types of immunological methods may be applied to HCP analysis: Western blotting (WB) and immunoassay (IA), which includes techniques such as ELISA and sandwich immunoassay or similar methods using radioactive, luminescent, or fluorescent reporting labels. Compositions of the present invention may include host cell protein of less than about 500, less than about 400, less than about 300, less than about 200, less than about 100 or less than about 50 ng/mg total protein.

Determination of Host Cell DNA.

Purity can be characterized in relation to the levels of host cell DNA. Detection of residual host cell DNA may be performed by Polymerase Chain Reaction (PCR) with a variety of primers for sequences in the host cell genome. Residual host cell DNA is generally reported as being below a certain threshold level, but may also be quantitated with a rPCR method. Compositions of the present invention may include host cell deoxyribonucleic acid (DNA) of less than about 100, less than about 90, less than about 80, less than about 70, less than about 60, less than about 50, less than about 40, less than about 30, less than about 20, or less than about 10 pg/mg total protein.

Endotoxin Testing.

Endotoxin is extremely potent, is heat stable, passes sterilizing membrane filters and is present everywhere bacteria are or have been present. An Endotoxin Unit (EU) is a unit of biological activity of the USP Reference Endotoxin Standard.

The bacterial endotoxins test (BET) is a test to detect or quantify endotoxins from Gram-negative bacteria using amoebocyte lysate (white blood cells) from the horseshoe crab (Limulus polyphemus or Tachypleus tridentatus). Limulus amebocyte lysate (LAL) reagent, FDA approved, is used for all USP endotoxin tests. There are three methods for this test: Method A, the gel-clot technique, which is based on gel formation; Method B, the turbidimetric technique, based on the development of turbidity after cleavage of an endogenous substrate; and Method C, the chromogenic technique, based on the development of color after cleavage of a synthetic peptide-chromogen complex.

Two types of endotoxin tests are described in the USP <85> BET. Photometric tests require a spectrophotometer, endotoxin-specific software and printout capability. The simplest photometric system is a handheld unit employing a single-use LAL cartridge that contains dried, pre-calibrated reagents; there is no need for liquid reagents or standards. The FDA-approved unit is marketed under the name of Endosafe®-PTS™. The device requires about 15 minutes to analyze small amounts of sample, a 25 µL aliquot from CSP diluted in a sterile tube, and to print out results. In contrast, gel-clot methods require a dry-heat block, calibrated pipettes and thermometer, vortex mixer, freeze-dried LAL reagents, LAL Reagent Water (LRW) for hydrating reagents and depyrogenated glassware. In this clot test, diluted sample and liquid reagents require about an hour for sample and positive-control preparation and an hour's incubation in a heat block; results are recorded manually. Thus, the simplicity and speed of the automated system make it ideally suited to the pharmacy setting.

Purity SEC HPLC.

The degree of aggregation of rhKLK1 (isolated glycoform or mixture of glycoforms) may be determined by Size-exclusion chromatography (SEC), which separates particles on the basis of size. It is a generally accepted method for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time. In certain embodiments, the "purity" of a KLK1 polypeptide in a composition may be specifically defined. For instance, certain compositions may include a hKLK1 polypeptide that is at least about 80, at least about 85, at least about 90, at least about 91, at least about 92, at least about 93, at least about 94, at least about 95, at least about 96, at least about 97, at least about 98, at least about 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds. Certain compositions are also substantially free of aggregates (greater than about 95% appearing as a single peak by SEC HPLC). Certain embodiments are free of aggregates with greater than about 96%, about 97%, about 98%, or about 99%, appearing as a single peak by SEC HPLC.

In certain embodiments, the rhKLK1 low- or high-molecular weight glycoform, or mixture of glycoforms, may have one or more of the following determinations of purity: less than about 1 EU endotoxin/mg protein, less that about 100 ng host cell protein/mg protein, less than about 10 pg host cell DNA/mg protein, and/or greater than about 95% single peak purity by SEC HPLC.

Activity of rhKLK1 Glycoforms.

KLK1 is a serine protease which cleaves low-molecular-weight kininogen resulting in the release of kallidin (lys-bradykinin). This protease activity of isolated KLK1 glycoforms may be measured in an enzyme activity assay by measuring either the cleavage of low-molecular-weight kininogen, or the generation of lys-bradykinin. In one assay format, a labeled substrate is reacted with the KLK1 glycoform, and the release of a labeled fragment is detected. One example of such a fluorogenic substrate suitable for KLK1 measurement of activity is D-val-leu-arg-7 amido-4-trifluoromethylcoumarin (D-VLR-AFC, FW 597.6) (Sigma, Cat #V2888 or Ana Spec Inc Cat #24137). When D-VLR-AFC is hydrolyzed, the free AFC produced in the reaction can be quantified by fludrometric detection (excitation 400 nm, emission 505 nm) or by spectrophotometric detection at 380 nm (extinction coefficient=12,600 at pH 7.2). Other methods and substrates may also be used to measure KLK1 glycoform proteolytic activity.

KLK1 activity, measured in Units or Units/ml, may be determined by comparing the relative activity of a KLK1 sample to the porcine kininogenase standard acquired from the National Institute for Biological Standards and Control (NIBSC Product No. 78/543). For this standard, the assigned potency is 22.5 international units (IU) per 20 µg ampoule of porcine pancreatic kininogenase. Typically, serial dilutions are made of the standard, and the activity in an unknown sample of KLK1 is compared to the standard. For experiments described herein, the rhKLK1 glycoforms or mixtures had specific activities of approximately 200 to 450 IU/mg, though specific activities of certain lots may be outside this range. However, the specific activity of rhKLK1 may vary from lot to lot, and thus would need to be checked to determine the dosage in mg/kg or total mg of rhKLK1 to administer to an animal or patient.

Animal based assays may also be used to determine the activity of hKLK1 glycoforms, including stimulating the uptake of glucose from the circulation in an animal. For example, the KLK1 glycoform may be administered to an animal that is responsive to KLK1, such as Sprague-Dawley rat, and glucose uptake by the tissues determined by an hyperinsulinemic-euglycemic clamp. Results of such animal based assays may be difficult to quantitate. As such, results from animal testing may be used in a qualitative manner such as comparing glycoforms to determine if certain glycoforms or mixtures have more or less activity compared to other glycoforms/mixtures.

The present invention also includes pharmaceutical compositions including a therapeutically effective amount of mixture of KLK1 glycosylated isoforms described herein, and a pharmaceutically acceptable diluent, adjuvant or carrier. Such pharmaceutical compositions may be formulated with pharmaceutically acceptable carriers or excipients, for instance, to optimize stability and achieve isotonicity. In certain aspects, the pH of the formulation may be near physiological pH or about pH 7.4, including about pH 6.5, about 7.0, about 7.1, about 7.2, about 7.3, about 7.4, about 7.5, about 7.6, about 7.7, about 7.8, about 7.9, about 8.0, about 8.5, or any range thereof. In some embodiments, a composition (e.g., pharmaceutical composition) comprises a KLK1 polypeptide in combination with a physiologically acceptable carrier. Such carriers include pharmaceutically acceptable carriers, excipients, or stabilizers which are nontoxic to the cell or mammal being exposed thereto at the dosages and concentrations employed. Methods of formulation are well known in the art and are disclosed, for example, in Remington: The Science and Practice of Pharmacy, Mack Publishing Company, Easton, Pa., Edition 21 (2005).

The phrase "physiologically-acceptable" or "pharmaceutically-acceptable" refers to molecular entities and compositions that do not produce a significant allergic or similar untoward reaction when administered to a human. Typically, such compositions are prepared as injectables, either as liquid solutions or suspensions; solid forms suitable for solution in, or suspension in, liquid prior to injection can also be prepared. The preparations can also be emulsified.

As used herein, "carrier" includes any and all solvents, dispersion media, vehicles, coatings, diluents, isotonic and absorption delaying agents, buffers, carrier solutions, suspensions, colloids, and the like. Except insofar as any conventional media or agent is incompatible with the active ingredient, its use in the therapeutic compositions is contemplated.

The KLK1 compositions described herein may be formulated for administered by a variety of techniques, including, for example, subcutaneous, intravenous, oral, rectal, transmucosal, transdermal, intestinal, parenteral, intramuscular, intramedullary, intrathecal, direct intraventricular, intraperitoneal, intranasal, and intraocular administration, among others.

Some embodiments include administration by subcutaneous infection. A subcutaneous injection (abbreviated as SC, SQ, sub-cu, sub-Q or subcut with SQ being the preferred abbreviation) can be administered as a bolus into the subcutis, the layer of skin directly below the dermis and epidermis, collectively referred to as the cutis. Exemplary places on the body where people can inject SC most easily include, without limitation, the outer area of the upper arm, just above and below the waist, excepting in certain aspects the area right around the navel (a ~2-inch circle), the upper area of the buttock, just behind the hip bone, and the front of the thigh, midway to the outer side, about 4 inches below the top of the thigh to about 4 inches above the knee. These areas can vary with the size of the person. Also, changing the injection site can prevent lumps or small dents called lipodystrophies from forming in the skin.

Subcutaneous injections usually go into the fatty tissue below the skin and in certain instances can utilize a smaller, shorter needle. In specific instances, a needle that is about ½ inch to about ⅝ of an inch in length with a gauge of about 25 to about 31 is sufficient to subcutaneously administer the medication. As will be appreciated by someone skilled in the art, these are general recommendations and SC injections may be administered with needles of other sizes. In some embodiments SC administration is performed by pinching-up on the tissue to prevent injection into the muscle, and/or insertion of the needle at a ~45° angle to the skin.

Intramuscular injection is injection into the substance of a muscle, usually the muscle of the upper arm, thigh, or buttock. Intramuscular injections are given when the substance is to be absorbed quickly. They should be given with extreme care, especially in the buttock, because the sciatic nerve may be injured or a large blood vessel may be entered if the injection is not made correctly into the upper, outer quadrant of the buttock. The deltoid muscle at the shoulder is also used, but less commonly than the gluteus muscle of the buttock; care must be taken to insert the needle in the center, 2 cm below the acromion. Injections into the anterolateral aspect of the thigh are considered the safest because there is less danger of damage to a major blood vessel or nerve. The needle should be long enough to insure that the medication is injected deep info the muscle tissue. As a general rule, not more than 5 ml is given in an intramuscular injection for an adult. The needle is inserted at a 90-degree angle to the skin.

Intraperitoneal injections are not commonly performed in human patients due to discomfort, and are administered to obtain systemic blood levels of the agent; faster than subcutaneous or intramuscular injection and used when veins not accessible. The needle is introduced into the upper flank and the syringe plunger withdrawn to ensure that intestine has not been penetrated. The injected solution should run freely.

Intravitreal (intraocular) injections are injections into the eye and a small volume of injection is essential for these types of injections to avoid hypertension in the eye. The site of injection is usually inferotemporal for ease of access. Some retina specialists will do the injection in the superotemporal quadrant, as they feel that should a complication such as a retinal detachment form, it can be easier treated with a pneumatic retinopexy.

Intracerebral injection is an injection into the cerebellum or brain. Such injections would require a small injection volume to avoid localized hypertension that may result in damage to neuronal tissue.

Intraspinal (intrathecal) injection is the injection of a substance through the theca of the spinal cord into the subarachnoid space.

The dosing of rhKLK1 glycoform mixtures will depend on various factors, including the disease to be treated, other medications that the patient is taking, etc. Dosing of KLK1 is also dependent on the specific activity of the KLK1 protein. Dosages of KLK1 are administered based on the number of units, which are converted into mg of protein. KLK1 is a serine protease which cleaves low-molecular-weight kininogen resulting in the release of kallidin (lys-bradykinin). This activity of KLK1 may be measured in an enzyme activity assay described above, or other methods and substrates may also be used to measure KLK1 proteolytic activity.

According to the FDA Guidance for Industry; Estimating the Maximum Safe Starting Dose in Initial Clinical Trial for Therapeutics in Adult Healthy Volunteers (July 2005), Appendix D: Converting animal doses to human equivalent doses. A human equivalent dose is ⅐ the rat dose and a human equivalent dose is 1/12 a mouse dose.

As one non-limiting example, in some aspects, a KLK1 mixture of glycoforms is subcutaneously administered at a dose of at least about 200 µg/kg (0.20 mg/kg), or in range of about 20 µg/kg to about 5000 µg/kg (0.02 to 5.0 mg/kg). As one illustrative example, if rhKLK1 is administered at a dose of about 200 ng/kg into a 90 kg patient, then a total of about 18.0 mg of KLK1 would be required. If the KLK1 is formulated at 5 mg/mL, then a total of about 3.6 mL would be injected, which is a large volume and could cause discomfort if injected subcutaneously. However, if the KLK1 is formulated at 25 mg/mL, the total injection volume is 0.72 mL, which is within the recommended injection volume for subcutaneous delivery of 1.0 to 1.5 mL.

Alternatively, to administer a dose of 500 µg/kg to a 90 kg person equates to about 45 mg of KLK1. If the KLK1 is formulated at 25 mg/mL, the injection volume is about 1.8 mL, which is above the recommended volume for subcutaneous injection. If the KLK1 is formulated at 50 mg/mL, the injection volume is about 0.9 mL or within the tolerable limit for subcutaneous injection into a human.

A composition of the present invention may include one or more additional therapeutic modalities. In some aspects, the administration of a composition of the present disclosure may allow for the effectiveness of a lower dosage of other therapeutic modalities when compared to the administration of the other therapeutic modalities alone, providing relief from the toxicity observed with the administration of higher doses of the other modalities. One or more additional therapeutic agents may be administered before, after, and/or coincident to the administration of agents of the present disclosure. Agents of the present disclosure and additional therapeutic agents may be administered separately or as part of a mixture of cocktail. As used herein, an additional therapeutic agent may include, for example, an agent whose use for the treatment of diabetes is known to the skilled artisan.

A KLK1 compositions as described herein may also be administered in combination with other drugs. A KLK1 composition described herein may be used to treat a patient with diabetes such as type 1 diabetes or type 2 diabetes and the subject many be administered a KLK composition and a known diabetes drug, known in the art to be useful in the treatment or prevention of insulin resistance and diabetes. Examples of diabetes drugs, include, for example, an antioxidant (such as vitamin E, vitamin C, an isoflavone, zinc, selenium, ebselen, or a carotenoid); an insulin or insulin analogue (such as regular insulin, lente insulin, semilente insulin, ultralente insulin, detemir, glargine, degludec, NPH or Humalog); an α-adrenergic receptor antagonist (such as prazosin, doxazocin, phenoxybenzamine, terazosin, phentolamine, rauwolscine, yohimbine, tolazoline, tamsulosin, or terazosin); a β-adrenergic receptor antagonist (such as acebutolol, atenolol, betaxolol, bisoprolol, carteolol, esmolol, metoprolol, nadolol, penbutolol, pindolol, propanolol, timolol, dobutamine hydrochloride, alprenolol, bunolol, bupranolol, carazolol, epanolol, moloprolol, oxprenolol, pamatolol, talinolol, tiprenolol, tolamolol, or toliprolol); a non-selective adrenergic receptor antagonist (such as carvedilol or labetolol); a first generation sulphonylurea (such as tolazamide, tolubtuamide, chlorpropamide, acetohexamide); a second generation sulphonylurea (such as glyburide, glipizide, and glimepiride); a biguanide agent (such as is metformin); a benzoic acid derivative (such as replaglinide); a α-glucosidase inhibitor (such as acarbose and miglitol); a thiazolidinedione (such as rosiglitazone, pioglitazone, or troglitazone); a phosphodiesterase inhibitor (such as anagrelide, tadalfil, dipyridamole, dyphylline, vardenafil, cilostazol, milrinone, theophylline, or caffeine); a cholineresterase antagonist (such as donepezil, tacrine, edrophonium, demecarium, pyridostigmine, zanapezil, phospholine, metrifonate, neostigmine, or galathamine); a glutathione increasing compound (such as N-acetylcysteine, a cysteine ester, L-2-oxothiazolidine-4-carboxolate (OTC), gamma glutamylcysteine and its ethyl ester, glytathtione ethyl ester, glutathione isopropyl ester, lipoic acid, cysteine, methionine, or S-adenosylmethionine); or incretin or incretin mimetics (such as GLP-1, GLP-2, glucagon like peptide analogues, such as DAC:GLP-1(CJC-1131), Liraglutide, ZP10, BIM51077, LY315902, LY307161 (SR), and exenatide). In some embodiments, the hKLK1 compositions are administered to a subject with insulin or an incretin mimetic.

The present invention includes methods of treating a subject in need thereof, comprising administering to the subject an effective amount of a composition as described herein. In some embodiments, the subject has established type 1 diabetes (T1D) or type 2 diabetes (T2D). In some embodiments, the subject is in the honeymoon phase, with the recent onset or diagnosis of type 1 diabetes T1D. The honeymoon, or remission phase, refers to the period following initial diagnosis when the remaining insulin producing beta cells are functioning well. During this honeymoon, it is easier to control blood sugars, with fewer swings, less risk for hypoglycemia, and lower overall average blood-sugar levels. The honeymoon period in type I diabetic patients is characterized by the preserved B cell function. In some embodiments, the subject in the honeymoon phase or recent onset of T1D has about 10-20% of their pancreatic beta cells relative to a healthy control and produces insulin. In some instances, the subject does not have type 1 diabetes (T1D) but is at risk for developing T1D. In some embodiments, the subject has latent autoimmune diabetes of adults (LADA). Type 2 diabetes (T2D) as used herein is a disease characterized by above normal levels of blood glucose. T2D may be caused by insufficient production of insulin in the subject or the subject being resistant to the action of insulin (insulin resistant). Administration of the compositions described herein to a subject with T2D may aid in moderating blood glucose levels.

In some embodiments, a therapeutically effective amount of a KLK1 composition includes an amount that lowers fasting glucose, increases glucose tolerance, or other indicator in a subject with diabetes. In some embodiments, a therapeutically effective dose is the amount of KLK1 glycoform composition that treats or delay the onset of type I diabetes without adverse side effects on blood pressure and heart rate.

In some embodiments, the subject has an ischemic condition. Non-limiting examples include cardiac ischemia (myocardial ischemia), ischemic colitis, brain ischemia (ischemic stroke), limb ischemia, and cutaneous ischemia. These and related medical conditions can be diagnosed according to routine techniques in the art.

The compositions of the present disclosure can be administered by any suitable means including, but not limited to, for example, oral, rectal, nasal, topical (including, for example, transdermal, aerosol, buccal and sublingual), vaginal, parenteral (including, for example, subcutaneous, intramuscular, intravenous, intradermal, intravesical, intraperitoneal, intravitreal, intraocular, or intracerebral, intraspinal). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

Devices.

The present invention also includes devices that contain a composition described herein, including devices suitable for subcutaneous delivery. In some embodiments, the device is a syringe. In some embodiments, the syringe is attached to a hypodermic needle assembly, optionally comprising a protective cover around the needle assembly. In some embodiments, the needle may be about ½ inch to about ⅝ of an inch in length and has a gauge of about 25 to about 31. Certain embodiments thus include devices that attached or attachable to a needle assembly that is suitable for subcutaneous administration, comprising a KLK1 glycoform mixture-based composition described herein. For example, certain devices include a vial or syringe, optionally where the vial or syringe is attachable to or is attached to a hypodermic needle assembly. Also included are vials having a rubber cap, where a needle/syringe can be inserted into the vial via the rubber cap to withdraw the KLK1-based composition for subcutaneous administration.

In particular aspects, the device is a syringe that is attachable or attached to a hypodermic needle, and is packaged with one or more removable and/or permanent protective covers around the needle or needle assembly. For instance, a first removable protective cover (which is removed during administration) can protect a user or other person from the needle prior to administration, and a second protective cover can be put (i.e., snapped) into place for safe disposal of the device after administration.

In certain aspects, a device, optionally a disposable device, comprises an individual dose of a KLK1 of at least about 25 mg, or in the range of about 2 to about 500 mg. In some embodiments, the device comprises a dose of at least about 0.02 to about 5.0 mg/kg, at least about 0.02 to about 10 mg/kg. In some embodiments, the device comprises a dose of at least about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0 mg/kg.

In certain aspects, the KLK1 composition may be packaged to allow administration by the patient or to the patient in a home setting on a daily basis, several times a week, weekly basis, or less frequently. A KLK1 composition may be formulated in a multi-dose vial or a multi-dose/multiuse syringe, similar to formulations of insulin or human growth hormone. In a multi-dose vial, an amount sufficient for at least 2 administrations may be in a vial (for example, 50 mg, or in the range of about 5 to 1000 mg), and a needle and syringe are used to draw the required amount of KLK1 from the vial and inject into a patient. In a multi-dose or multiuse syringe contains an amount of KLK1 sufficient for at least 2 administrations (for example, 50 mg, or in the range of about 5 to 1000 mg), and the volume that may be injected may be determined by the patient. The multi-dose syringe may also have a replaceable cartridge that may be loaded into the syringe that contains additional amounts of KLK1 composition.

To determine if a dose of a KLK1 glycoform mixture of a defined ratio is effective in treating a patient, either in terms of the amount (number of units administered to a patient) of KLK1 glycoform administered or the frequency of administration, several markers may be measured. The following markers are described as examples in treating patients with T1D, and are not intended to be an exhaustive list. An effective dose of KLK1 glycoform may increase the numbers of T-regulatory cells in the spleen, specifically CD4+/CD25+/FoxP3+ cells in the spleen of subject with T1D. Another endpoint to determine the effective dose is an improvement in a hyperinsulinemic-euglycemic clamp test, as observed and described herein below. Another endpoint to determine the effective dose is a decreases in insulitis, which measured by pancreatic biopsies, or other non-invasive procedures in humans. As may be evident, in treating diseases other than T1D, other markers may be measured to determine if a dose of KLK1 glycoform or mixture thereof is effective in treating the disease.

For the treatment of subjects with T2D, the KLK1 glycoforms mixture composition is administered to the subject parameters are measured such as a decrease in glycated hemoglobin (HbA1c) decrease in fasting blood glucose levels. Other parameters may also be measured to determine if the dose of rhKLK1 glycoform mixtures is effective in treating T2D.

Based on the results of the markers being measured, the dosage amount of KLK1 glycoform or mixtures can be increased or decreased, merely by way of example, by about 1.1×, 1.2×, 1.3×, 1.4×, 1.5×, 1.6×, 1.7×, 1.8×, 1.9×, 2×, 2.5×, 3×, 3.5×, 4×, 4.5×, 5×, 6×, 7×, 8×, 9×, 10×, 15×, 20× or more, relative to the previous dosage. The dosage frequency can be increased or decreased, merely by way of illustration, by about 1, 2, 3, 4, 5 or more dosages per day, and/or 1, 2, 3, 4, 5, 6, 7, 8, 9, 10 or more dosages per week, relative to the previous dosing schedule. As noted above, the dosage amount can be increased or decreased separately or in combination with the dosage frequency, and vice versa, optionally until a desired level or range of one or more biomarkers or other treatment indicators is achieved.

A composition of the present invention may be endotoxin free or substantially endotoxin free. As sued herein, the term "endotoxin free" or "substantially endotoxin free" relates generally to compositions, solvents, devices, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing KLK1 polypeptides in and isolating them from eukaryotic cells such as mammalian cells to reduce, if not eliminate, the risk of endotoxins being present in a composition of the invention. Preferred are methods of producing KLK1 polypeptides in and isolating them from recombinant cells grown in chemically defined, serum free media.

Endotoxins can be detected using routine techniques known in the art. For example, the Limulus Ameobocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml, or EU/mg protein. Typically, 1 ng lipopolysaccharide (LPS) corresponds to about 1-10 EU.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount or level produced by a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount or level produced a control composition, sample or test subject.

As one non-limiting example, the comparison can be between the amount or level of a pharmacokinetic parameter or biological/therapeutic response produced by administration of one mixture of triple:double glycosylated isoforms (or glycoforms) of KLK1 (for example, about 55:45, about 50:50, or about 45:55) relative to administration of a different mixture of such glycoforms (for example, about 60:40, about 40:60, ~90:10, ~10:90, ~95:5, or ~5:95). As another non-limiting example, the comparison can be between amount or level of a pharmacokinetic parameter or biological/therapeutic response produced by administration of a substantially pure composition of a triple glycosylated isoform (or glycoform) of rhKLK1 (for example, about 90%, about 95% triple glycosylated) relative to administration of a different glycoform (for example, about 90%, about 95% double glycosylated) or a mixture of glycoforms (for example, about 60:40 or about, 40:60).

Other examples of comparisons and "statistically significant" amounts are described herein. A result is typically referred to as "statistically significant" if it is unlikely to have occurred by chance. The significance level of a test or result relates traditionally to the amount of evidence required to accept that an event is unlikely to have arisen by chance. In certain cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see Goodman, Ann Intern Med. 130:1005-13, 1999).

The term "solubility" refers to the property of a rhKLK1 polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 6.0, pH 7.0, pH 7.4, pH 8.0 or pH 9.0. In certain embodiments, solubility is measured in water or a physiological buffer such as PBS or NaCl (with or without NaP), In specific embodiments, solubility is measured at relatively lower pH (for example, pH 6.0) and relatively higher salt (for example, 500 mM NaCl and 10 mM NaP). In certain embodiments, solubility is measured in a biological fluid (solvent) such as blood or serum. In certain embodiments, the temperature can be about room temperature (for example, about 20, about 21, about 22, about 23, about 24, or about 25° C.) or about body temperature (37° C.). In certain embodiments, a KLK1 polypeptide has a solubility of at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, or at least about 60 mg/ml at room temperature or at 37° C.

"Substantially" or "essentially" means nearly totally or completely, for instance, 95%, 96%, 97%, 98%, 99% or greater of some given quantity.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

A "subject," as used herein, includes any animal that exhibits a symptom, or is at risk for exhibiting a symptom, which can be treated with a KLK1 polypeptide or composition of the present invention. Suitable subjects (patients) include laboratory animals (such as mouse, rat, rabbit, or guinea pig), farm animals, and domestic animals or pets (such as a cat or dog). Non-human primates and, preferably, human patients, are included.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances such as host cell proteins or nucleic acids.

The present invention is illustrated by the following examples. It is to be understood that the particular examples, materials, amounts, and procedures are to be interpreted broadly in accordance with the scope and spirit of the invention as set forth herein.

EXAMPLES

Example 1

A cDNA coding for pre-pro-human KLK1, the 262 amino acid residue sequence depicted in SEQ ID NO:2, was purchased from OriGene™ (Rockville, Md., USA). The KLK1 cDNA (Catalogue No. SC122623) is a human cDNA open reading frame clone, cloned into the multi-cloning site of OriGene's pCMV6-XL5 vector, between a cytomegalovirus (CMV) promoter to control transcription of cDNA coding for pre-pro-human KLK1 and a polyadenylation signal. This KLK1 clone was sequenced and, using translation software, translated to reveal SEQ ID NO:2. This sequence differed at 2 amino acid residues from the human KLK1 sequence in GenBank as Ref No. NP_002248.1 (SEQ ID NO:1). As depicted in SEQ ID NO:2, single nucleotide polymorphisms (SNP's) resulted in an E to Q change at amino acid residue 145 of 262, and an A to V change at amino acid position 188 of 262. All subsequent experiments were performed with KLK1 having the amino acid sequence in SEQ ID NO:2.

The human KLK1 cDNA in the pCMV6-XL5 was transfected into a CHO cell line using the FreeStyle™ MAX CHO Expression System (Invitrogen, Carlsbad, Calif. Catalog no. K9000-20). The kit allowed for transient transfection of vectors into Chinese Hamster Ovary (CHO) cells, growth of the transfected CHO cells in 10 liter culture, and protein expression in defined, serum-free medium. The CHO cells are grown in suspension and transient transfection of the KLK1 vector was performed with the liposome reagent supplied in the kit as per instructions.

Expression and purification of recombinant human KLK1 were performed essentially as described by Hsieng S. Lu, et al, (Purification and Characterization of Human Tissue Pro-kallikrein and Kallikrein Isoforms Expressed in Chinese Hamster Ovary Cells, *Protein Expression and Purification* (1996), 8, 227-237). Briefly, following transfection and allowing sufficient time for expression of recombinant human KLK1, culture supernatant from the 10 liter culture of CHO cells was harvested by centrifugation followed by 0.2 micron filtration. Clarified supernatant was then concentrated, reacted with trypsin to activate the recombinant human KLK1. Because the transient transfection was performed with the cDNA coding for pre-pro-human KLK1, the recombinant human KLK1 secreted from the CHO cells was in an inactive proprotein form. Therefore, activity assay of cell culture supernatant KLK1 involves an activation step with trypsin digestion. Activation is done with trypsin at 10 nM final concentration for 2 hours at room temperature, and the trypsin inactivated with Soybean Trypsin Inhibitor.

Following activation of the recombinant human KLK1, ammonium sulphate was added to the supernatant, and it was loaded onto an Octyl Sepharose® column. The Octyl column elution pool of active KLK1 was further purified by Benzamidine affinity column. Pooled active fractions off the Benzamidine column were then buffer exchanged into DEAE equilibration buffer and polished by DEAE column. Active KLK1 fractions from DEAE were pooled and buffer exchanged into 1×PBS buffer. The final KLK1 bulk drug substance was aliquoted and stored at −20° C.

Example 2

Figure 2:
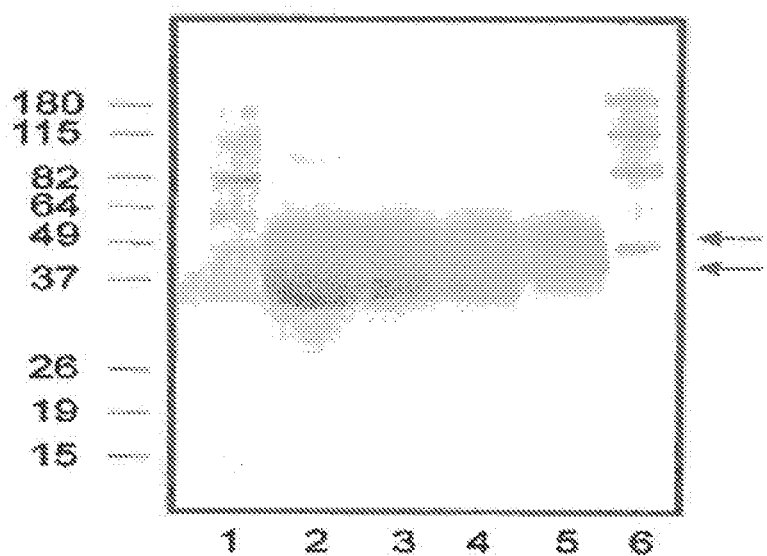
FIG. 2 is a Western blot stained with mouse anti-human KLK1 polyclonal antibodies of various amounts of recombinant human KLK1 purified from CHO or 293 cell lines following transient transfection. Lanes 1 and 6 are loaded with a pre-stained protein ladder, the molecular weights of the standards are written on the side (in kDa). Lanes 2-5 have KLK1 purified from CHO cells (lane 2—5 µl protein; lane 3—2.5 µl protein; lane 4—1.25 µl protein). Lane 5 has 2.5 µl of KLK1 protein purified from transient transfection of 293 cells.

The purified recombinant human KLK1 contained approximately 30% carbohydrate content based on the molecular weight estimated by sodium dodecyl sulphate (SDS) polyacrylamide gel electrophoresis (see FIG. 1). KLK1 from CHO cells appears as a band having an apparent molecular weight of ~40 to 49 kDa; such a broad band may result from different glycosylated isoforms of KLK1 secreted by CHO cells. For KLK1 expressed in 293 cells, two bands appeared on the SDS-PAGE gel at approximately 40 kDa and 45 kDa. The identity of the bands as human KLK1 was confirmed by Western blot analysis using mouse polyclonal antibody raised against a full-length human KLK1 protein (Catalog #: H00003816-B01P, KLK1 purified MaxPab mouse polyclonal antibody (B01P), Abnova Corporation, Walnut, Calif., USA) (see FIG. 2). The Western blot confirms the results of the SDS-PAGE gel, in that recombinant human KLK1 from CHO cells appears as a band having an apparent molecular weight of ~40 to 49 kDa, and KLK1 expressed in 293 cells resolves as two bands at approximately 40 kDa and 45 kDa.

The purity of KLK1 from CHO was visually estimated from the SDS-PAGE gel to be >90% with a final concentration of 1.19 mg KLK1 protein/ml. From the SDS-PAGE gel, it appears CHO produced KLK1 also contains higher molecular weight impurities (~70-95 kDa) that are not visible in the 293 preparation.

An enzyme activity assay was used to test for activity of recombinant human KLK1 in cell culture supernatants, chromatography fractions during purification and in the final purified product. One fluorogenic substrate suitable for tissue kallikrein measurement of activity is D-val-leu-arg-7 amido-4-trifluoromethylcoumarin (D-VLR-AFC, FW 597.6) (Sigma, Cat #V2888 or Ana Spec Inc Cat #24137). When D-VLR-AFC is hydrolyzed, the free AFC produced in the reaction can be quantified by fluorometric detection (excitation 400 nm, emission 505 nm) or by spectrophotometric detection at 380 nm (extinction coefficient=12,600 at pH 7.2).

The measurement of recombinant human KLK1 activity (Units/ml) produced in the CHO cells was determined by comparing the relative activity of recombinant KLK1 to the kininogenase porcine standard acquired from the National Institute for Biological Standards and Control (NIBSC Product No. 78/543). For this standard, the assigned potency is 22.5 international units (IU) per 20 μg ampoule of porcine pancreatic kininogenase.

Example 3

Experiments were performed to determine if the Octyl Sepharose column is capable of resolving the high- and low-molecular weight forms of recombinant human KLK1, and to quantify the relative activity of the two isolated forms.

Approximately 45 mg (20 mL) of recombinant human KLK1 was subjected to the Octyl Sepharose column as detailed below (see Table 1):

Resin: Octyl Sepharose (GE) hydrophobic interaction resin.
Column: XK16×16, 1.6 cm×16 cm (diameter×length), 32 mL resin bed volume
Flow Rate: 3 mL/minute load (~10 minute contact time), 3 mL/minute gradient (~90 cm/hr).
Load: 20 mL (~44.6 mg) of purified recombinant human KLK1 diluted to 150 mL with 50 mM Sodium phosphate, 1.5M ammonium sulfate, pH 7.0.
Buffers: 50 mM Sodium phosphate, 1.5M ammonium sulfate, pH 7.0. 50 mM Sodium phosphate, pH 7.0.
Elution: Gradient from 0% to 67% B (50 mM Sodium phosphate, pH 7.0) over 5CV's (160 mL), followed by 90 mL at 67%.
Fractions: collected every 8 mL over the gradient elution.

TABLE 1

Octyl Sepharose Column Protocol

| Step | Buffer | CVs | Volume (mL) |
|---|---|---|---|
| Sanitization | 0.1M Sodium hydroxide (storage) | na | na |
| Equilibration | 1.5M Ammonium sulfate in 50 mM Sodium phosphate, pH 7.0 | >5 | 175 |
| Load | Purified recombinant human KLK1 in (A) | | 150 |
| Wash Buffer | 1.5M Ammonium sulfate in 50 mM Sodium phosphate, pH 7.0 | 5 | 160 |
| Elution | Gradient of 0% to 67% B over 160 mL (53.3 minutes), hold at 67% for ~3 cv's | 5<br>3 | 160<br>90 |
| Strip | 100% B (50 mM Sodium phosphate, pH 7.0) | ~5 | 150 |
| Clean and store | 0.1M NaOH | 3 | ~100 |

Figure 3A:
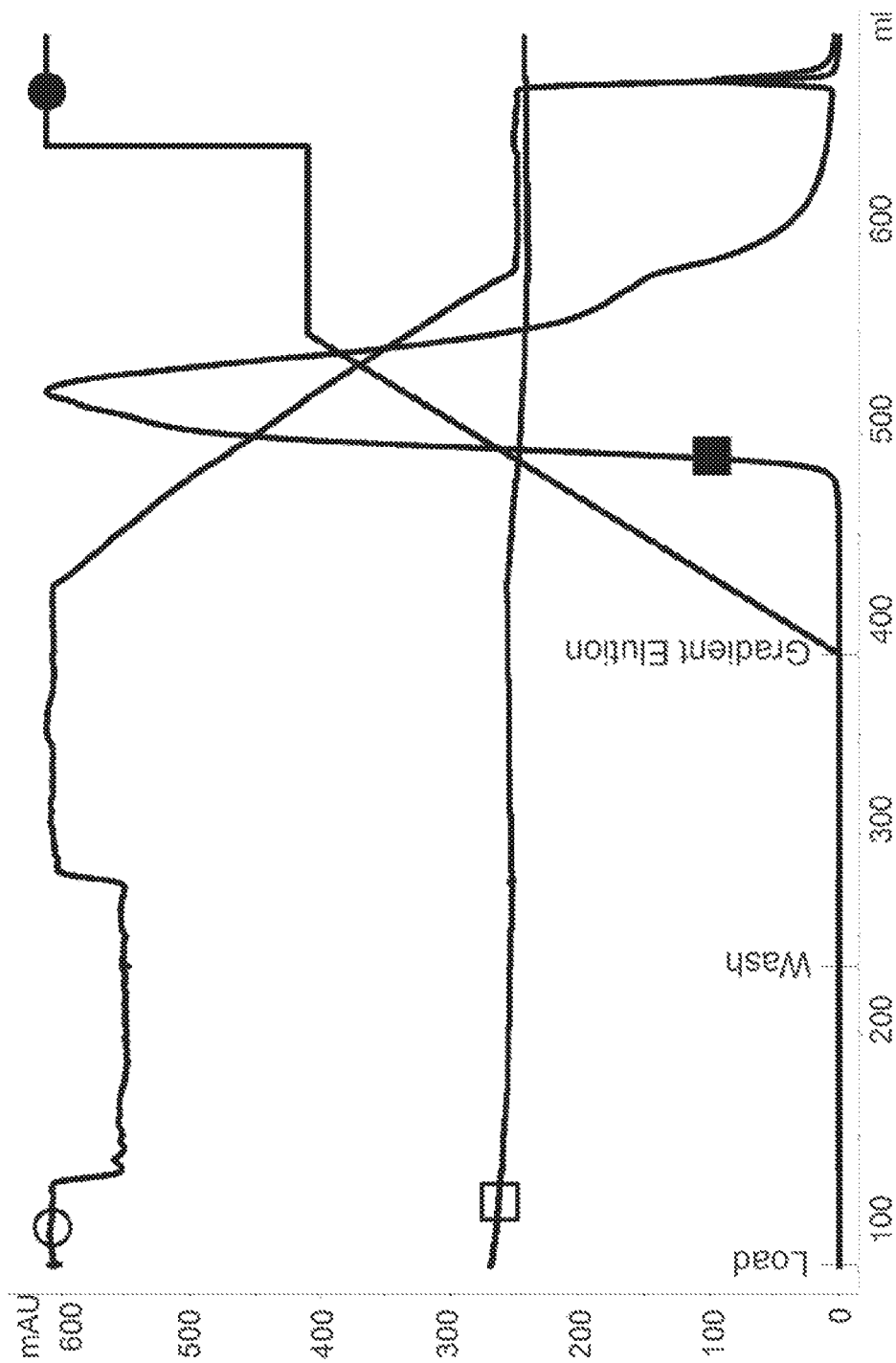
FIG. 3A is a chromatogram depicting the A280 absorbance of various elution fractions from the Octyl Sepharose hydrophobic interaction resin used to separate the low and high molecular weight recombinant human KLK1 glycoforms.
Figure 3B:
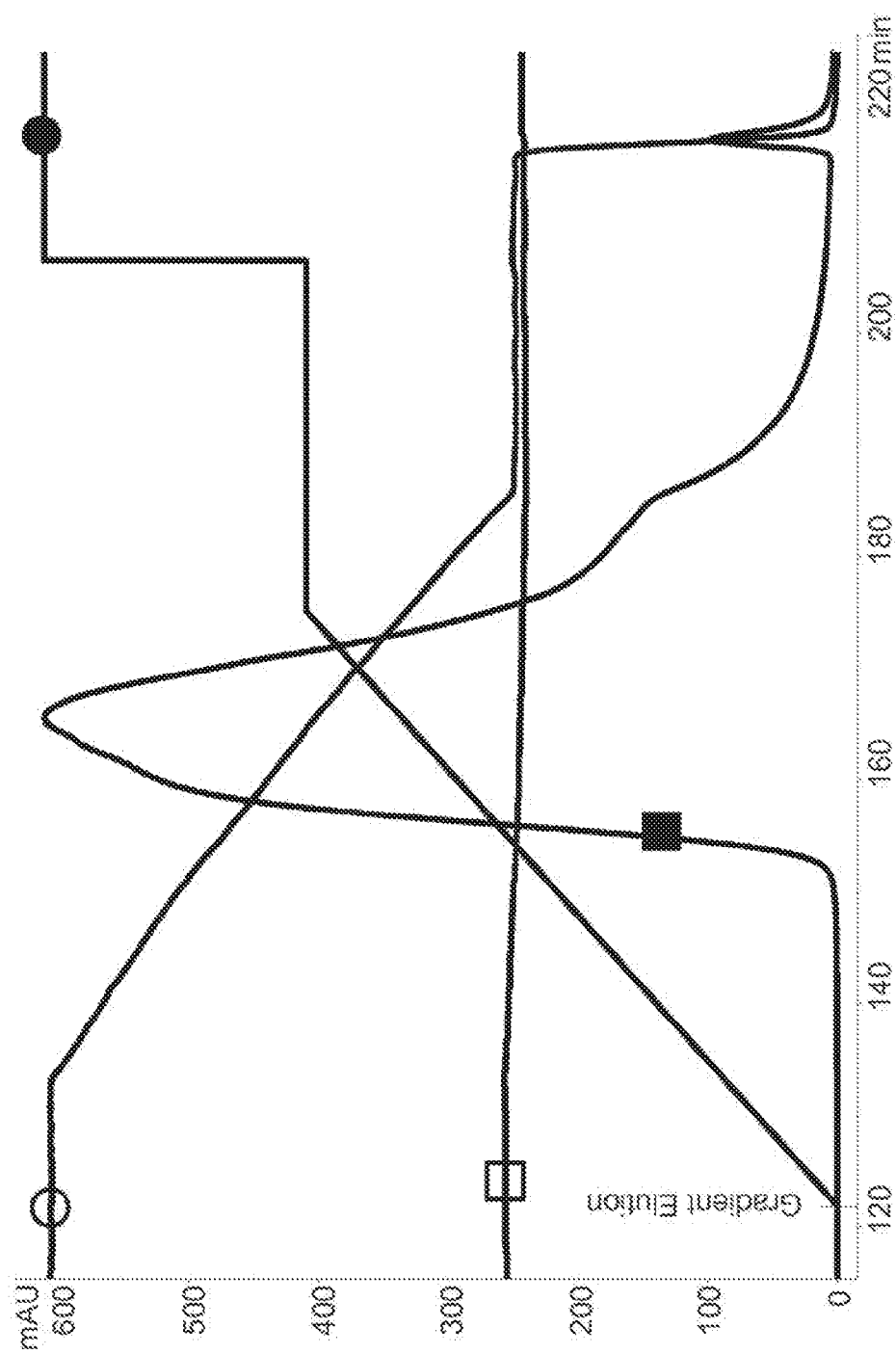
FIG. 3B is an enlargement of the peak shown in FIG. 3A. ■ represents protein concentration (measured at A280); ● represents % elution buffer; ○ represents % loading buffer/wash buffer; and ▲ represents pH of solution leaving column.
Figure 4:
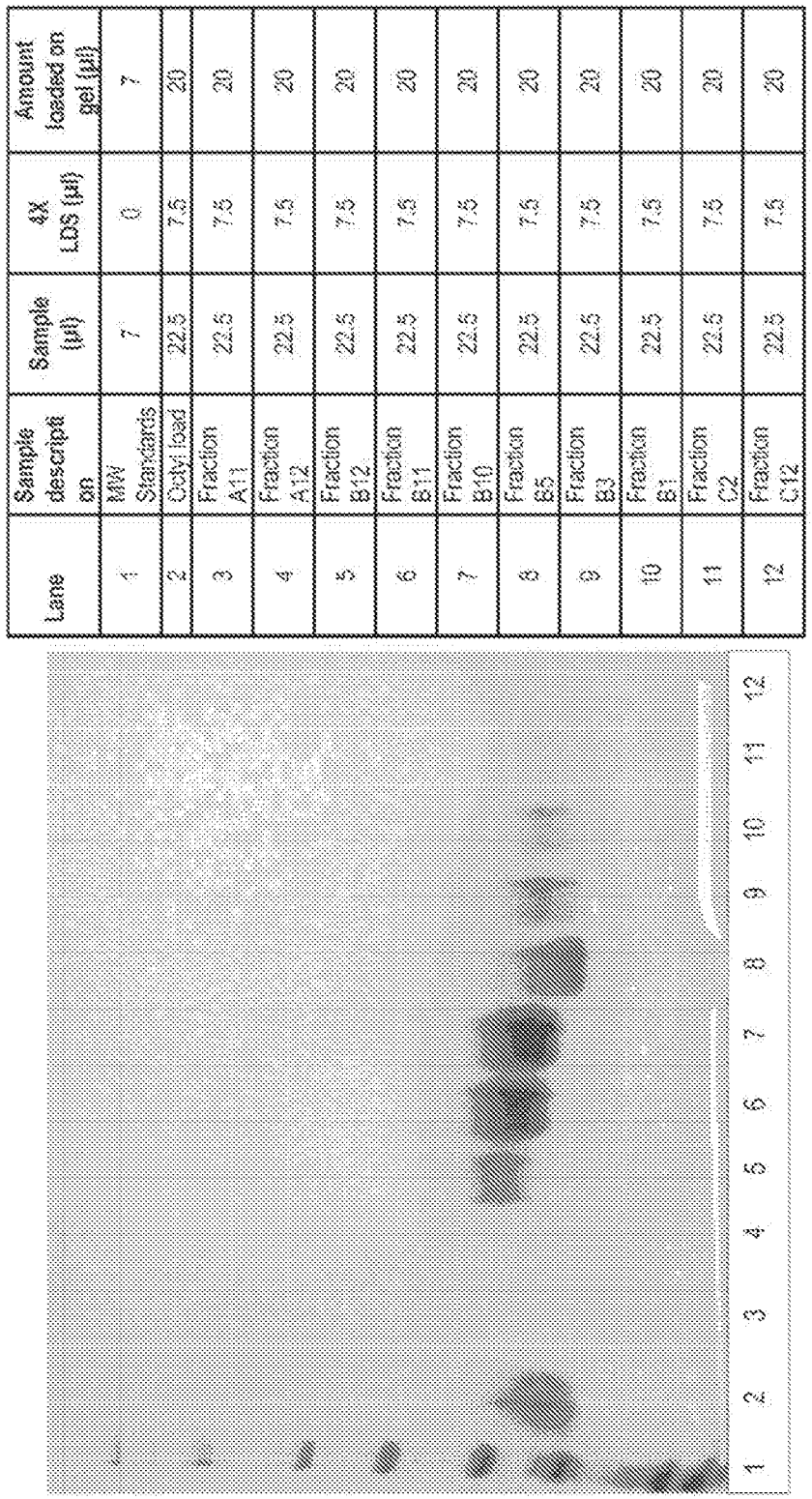
FIG. 4 is an SDS-PAGE of samples from the elution fractions from the Octyl Sepharose hydrophobic interaction resin used to separate the low and high molecular weight recombinant human KLK1 isomers.

The chromatogram in FIG. 3A (magnified in FIG. 3B) and the SDS-PAGE analysis in FIG. 4 illustrate that the low molecular weight KLK1 glycoform was isolated from the high molecular glycoform using the Octyl Sepharose column. All fractions were sterile filtered and stored at 2-8° C. pending analysis.

Figure 5A:
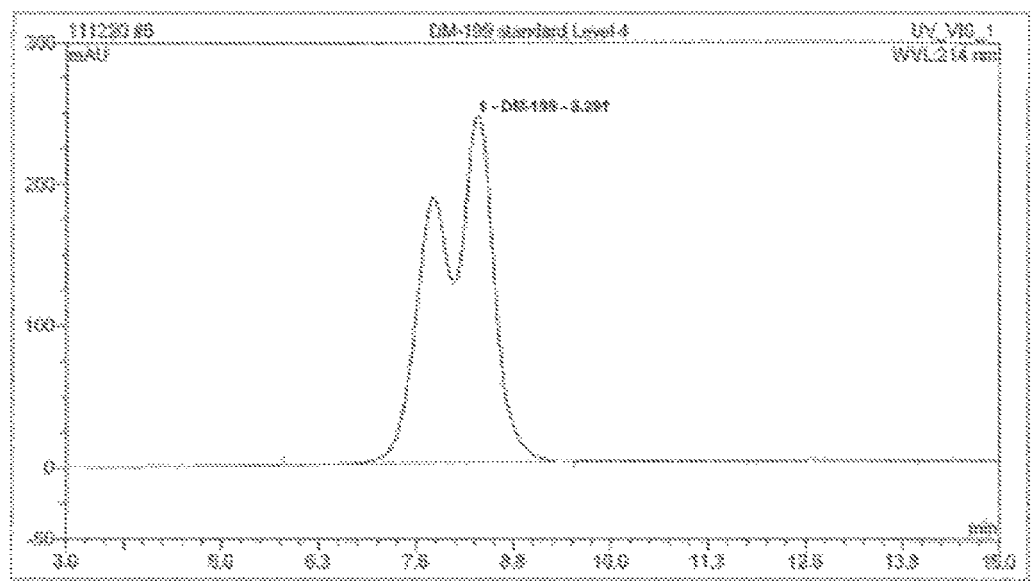
FIG. 5A is a chromatogram of RP-HPLC analysis of human KLK1 isolated from CHO cells depicting the mixture of low- and high molecular weight glycoforms (approximate ratio 45:55) of hKLK1.
Figure 5B:
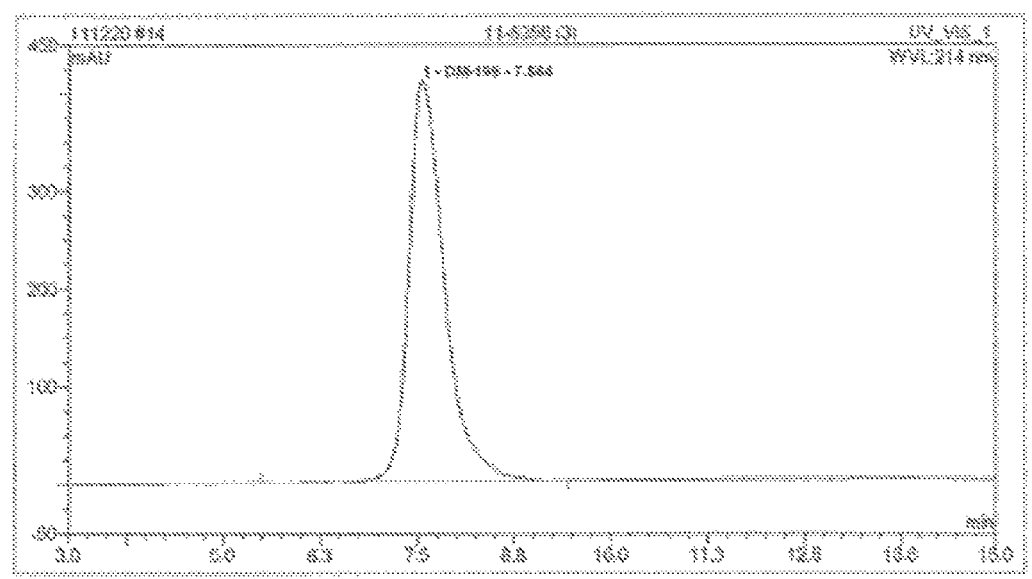
FIG. 5B is a chromatogram of RP-HPLC analysis of Fraction B11 (High molecular weight human KLK1 glycoform).
Figure 5C:
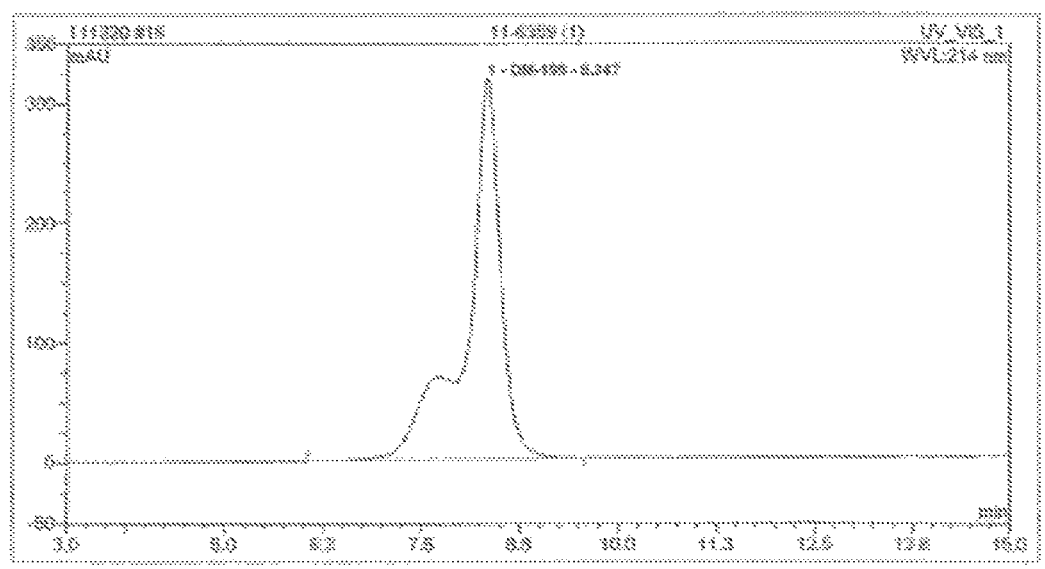
FIG. 5C is a chromatogram of RP-HPLC analysis of Fraction B5 (Low molecular weight human KLK1 glycoform).

Two fractions were identified for farther analysis, fraction B11 high molecular weight (triple glycosylated) rhKLK1 glycoform (FIG. 4, lane 6) and fraction B5 low molecular weight (double glycosylated) rhKLK1 glycoform (FIG. 4, lane 8). These two fractions were analyzed by absorbance, activity and reverse phase—high performance liquid chromatography (RP-HPLC). The fractions were aliquotted to 1 mL aliquots, labeled and frozen. Results of the testing are shown below. RP-HPLC quantitation correlates very well with A280 absorbance (using a 1.76 extinction coefficient) and shows the two rhKLK1 glycoforms, as seen with the Octyl chromatography results. Specifically, RP-HPLC analysis of recombinant human KLK1 prior to separation of the glycoforms appears as two peaks (FIG. 5A). Following separation of the glycoforms, RP-HPLC analysis fraction B11 (high molecular weight KLK1 glycoform) appears as a single band (FIG. 5B), and fraction B5 (low molecular weight KLK1 glycoform) appears a prominent band (FIG. 5C), though some contamination from the low molecular weight KLK1 glycoform is evident.

Figure 6:
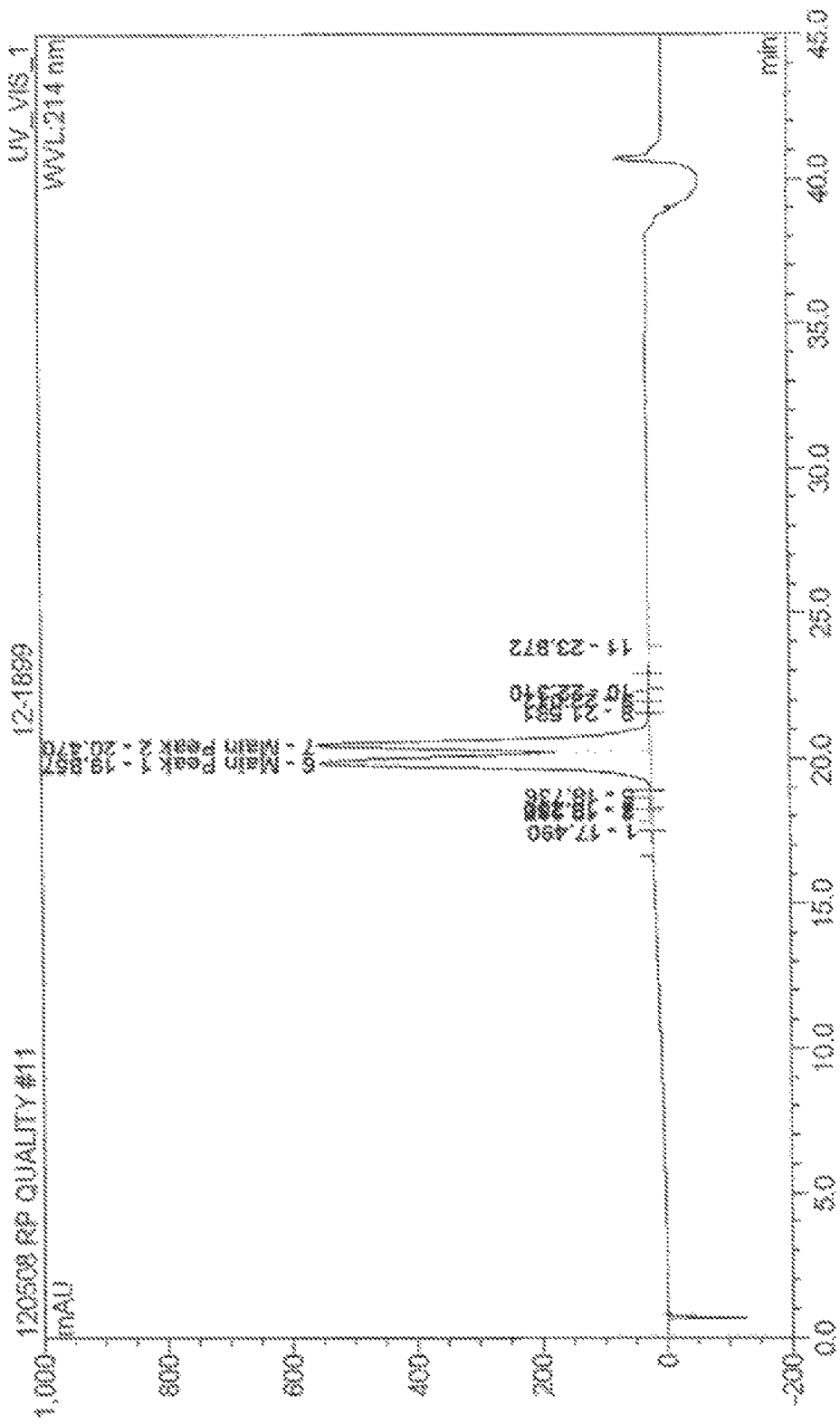
FIG. 6 is a chromatogram of RP-HPLC analysis of human KLK1 isolated from CHO cells depicting an approximate 50:50 mixture of low- and high molecular weight glycoforms of hKLK1.

Five cell lines were generated producing different ratios of the low and high molecular weight glycoforms of rhKLK1. FIG. 5A depicts a mixture of purified rhKLK1 with the low and high molecular weight KLK1 glycoforms at an approximate ratio of 55:45, respectively, and specifically 52% and 47.5% for the high- and low-molecular weight KLK1 glycoforms, respectively, and 0.5% as aggregates. rhKLK1 was also purified from another recombinant CHO cell line that was expressing rhKLK1 glycoforms at approximately a 50:50 ratio (sec FIG. 6).

Specific activity of KLK1 The specific activity (Units/mg) of the low-molecular weight, high-molecular weight rhKLK1 glycoforms, as well as the 50:50 mixture of rhKLK1 and human urinary KLK1, was tested by an enzyme activity assay. One fluorogenic substrate suitable for tissue kallikrein-1 measurement of activity is D-val-leu-arg-7 amido-4-trifluoromethylcoumarin (D-VLR-AFC, FW 597.6) (Sigma, Cat #V2888 or Ana Spec Inc Cat #24137). When D-VLR-AFC is hydrolyzed, the free AFC produced in the reaction can be quantified by fluorometric detection (excitation 400 nm, emission 505 nm according to the catalogue, but alternate excitation and emissions are possible, including excitation 360 nm, emission 460 nm) or by spectrophotometric detection at 380 nm (extinction coefficient=12,600 at pH 7.2).

The measurement of the specific activity (Units/mg) for the KLK1 glycoforms and mixtures was determined by comparing the relative activity of KLK1 to the kininogenase porcine standard acquired from the National Institute for Biological Standards and Control (NIBSC Product No. 78/543). For this standard, the assigned potency is 22.5 international units (IU) per 20 µg ampoule of porcine pancreatic kininogenase. All dosing of rats was based on units of KLK1.

Human urinary (HU) KLK1 purchased from Lee Biosciences (Catalog #: 314-15: CAS: 9001-01-8: Lot #: L23165). HU KLK1 is known to comprise a 60:40 glycoform ratio (high to low molecular weight). According to the product specification from the manufacturer, the HU KLK1 is >99% pure and has a specific activity of 9.9 U/mg. However, this determination of specific activity was with a different assay and under different conditions than the D-VLR-AFC assay described above. Therefore, HU KLK1 was tested in the D-VLR-AFC assay along with the low- and high molecular weight rhKLK1 glycoforms and 50:50 rhKLK1 mixture. The results of the specific activity calculations and the protein concentrations as determined by RP-HPLC or A280 nm are summarized in Table 2 below.

TABLE 2

| Fraction | Specific Activity | | |
|---|---|---|---|
| | A280 nm mg/mL | RP-HPLC mg/mL | Specific Acivity U/mg (A280 nm) |
| 50:50 mixture rhKLK1 | 0.22 | 0.49 | 454 |
| B11 (Lane 6) | 0.48 | 0.50 | 389 |
| B5 (Lane 8) | 0.36 | 0.39 | 289 |
| HU KLK1 | 1.0 | NA | 311 |

The purity of rhKLK1 (50:50 mixture, B5 and B11 fraction) was relatively low endotoxin to total protein (<1 EU/mg protein), low host cell protein to total protein (<100 ng/mg protein), low host cell DNA to total protein (<10 pg/mg protein), and mostly appeared as a monomer (<95% single peak by SEC HPLC). For HU KLK1 the endotoxin and degree of aggregation were not quantitated. However, qualitative testing suggested the HU KLK1 had endotoxin levels of >1 EU/mg protein, higher than for the rkKLK1 50:50 mixture, B5 and B11 fraction, and a greater degree of aggregation (>5%) than rhKLK1 (50:50 mixture, B5 and B11 fraction), the latter having aggregation levels of <5%.

Hyperinsulinemic-Euglycemic Clamp.

The in vivo activity, and specifically the ability to stimulate glucose uptake by tissues, of the two isolated glycoforms of rhKLK1, the 50:50 mixture of glycoforms and HU KLK1, were determined by a hyperinsulinemic-euglycemic clamp study. The hyperinsulinemic-euglycemic clamp is the gold standard for investigating glucose utilization, including quantifying insulin resistance because it measures the amount of glucose necessary to compensate for an increased insulin level without causing hypoglycemia. Increased glucose infusion rate detected in the clamp may also indicate increased insulin sensitivity, or increased uptake of glucose by muscles, adipocytes, or other tissues in the body.

A 120 minute hyperinsulinemic-euglycemic clamp assay was performed on 6 hours fasted Sprague Dawley rats with continuous infusion of human insulin (Humulin, Lilly) at a constant rate of 4 mU/kg/minute. At the same time 20% glucose solution at variable rate was infused and the rate adjusted every 10 minutes to maintain target blood glucose level. Both insulin and glucose were infused through catheterized right jugular vein and blood glucose levels were monitored from the catheterized left carotid artery.

Twelve groups of three rats each were used for this clamp procedure. Each group of four rats were injected subcutaneously with either rhKLK1, Fraction 11 (high molecular weight KLK1 glycoform), Fraction 5 (low molecular weight KLK1 glycoform), and human urinary KLK1 at 1.0 U, 0.33 U and 0.1 U/rat (see Table 3 below). The human KLK1 was dissolved in PBS and the rats were dosed subcutaneously, 30 minutes prior to the clamp procedure. Table 3 summarizes the dosing of rats with the various form of human KLK1.

TABLE 3

| Group | Compound | Dose |
|---|---|---|
| 1. rhKLK1 50:50 mixture | rhKLK1 | 1.0 U/rat |
| 2. rhKLK1 50:50 mixture | rhKLK1 | 0.33 U/rat |
| 3. rhKLK1 50:50 mixture | rhKLK1 | 0.1 U/rat |
| 4. High MW glycoform | rhKLK1 fraction B11 | 1.0 U/rat |
| 5. High MW glycoform | rhKLK1 fraction B11 | 0.33 U/rat |
| 6. High MW glycoform | rhKLK1 fraction B11 | 0.1 U/rat |
| 7. Low MW glycoform | rhKLK1 fraction B5 | 1.0 U/rat |
| 8. Low MW glycoform | rhKLK1 fraction B5 | 0.33 U/rat |
| 9. Low MW glycoform | rhKLK1 fraction B5 | 0.1 U/rat |
| 10. Urinary KLK1 | huKLK1 | 1.0 U/rat |
| 11. Urinary KLK1 | huKLK1 | 0.33 U/rat |
| 12. Urinary KLK1 | huKLK1 | 0.1 U/rat |

Figure 7:
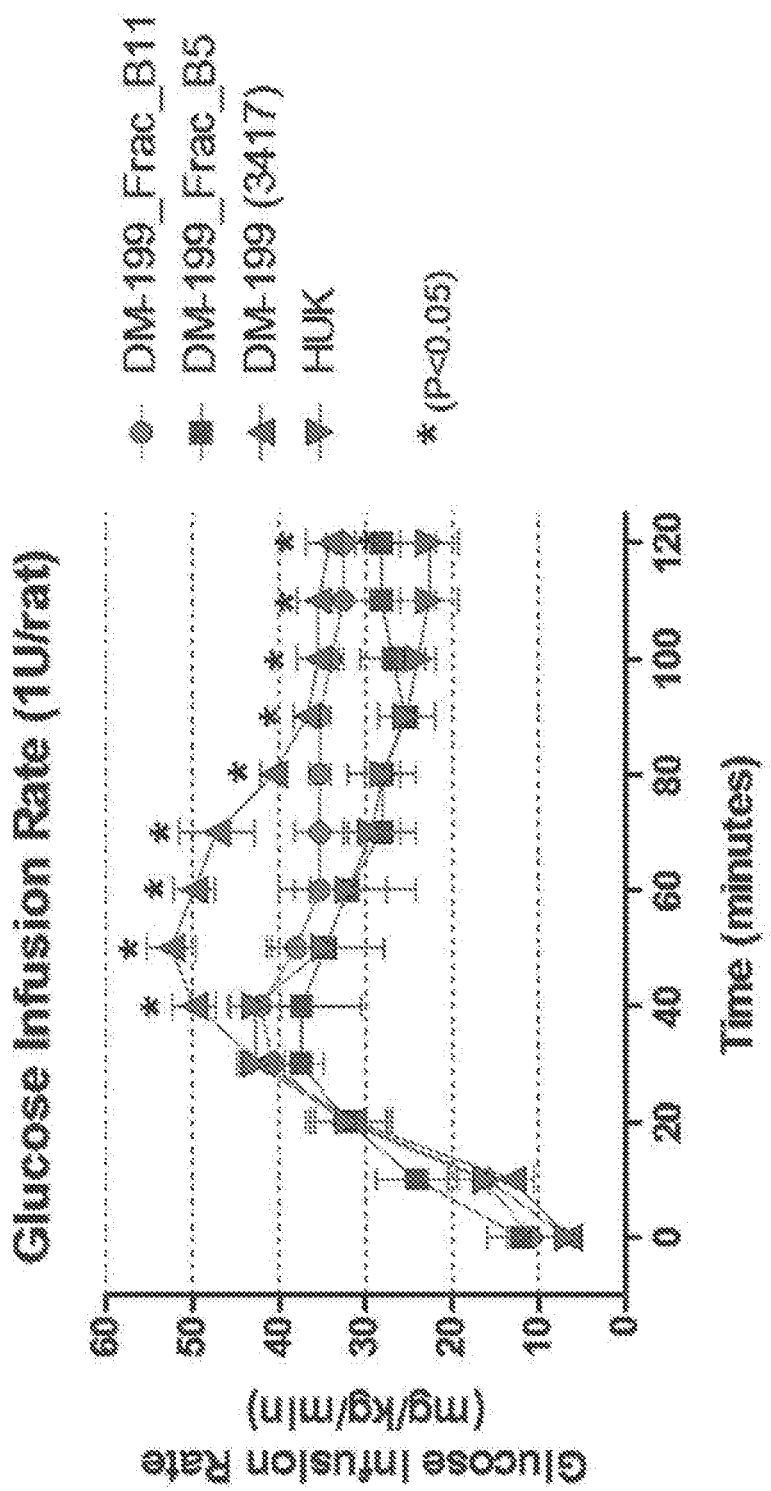
FIG. 7 is a graph of the glucose infusion rate in Sprague-Dawley rat during a hyperinsulinemic-euglycemic clamp, following administration of HU KLK1, rhKLK1, low molecular weight or high molecular weight KLK1 glycoforms.

Arterial blood glucose levels were monitored prior to dosing at t=−120, −190, −30, −15 and 0 minutes and then at every 10 minutes for 120 minutes (t=120), using Glucose meter (Accu Check, Roche Diagnostics). The clamps were continued for 120 minutes (t=120) whereby experiment was terminated. The effect of KLK1 glycoform administration on the rate of glucose infusion required to maintain equal blood glucose level was recorded. FIG. 7 is a graph of the glucose infusion rate (GIR) for rats treated with 1 U/rat of rhKLK1 (50:50 mixture), HU KLK1, or the low- or high molecular weight glycoform of rhKLK1. This graph is typical of the GIR graphs in that the GIR increases from time zero and peaks at about 40 to 60 minutes, and then there is a slight decrease in GIR. Further analysis was performed on the glucose infusion rate (GIR) to calculate the area under the curve (AUC), a measure of total glucose infused (mg/kg/min-min) during the clamp study.

Figure 8:
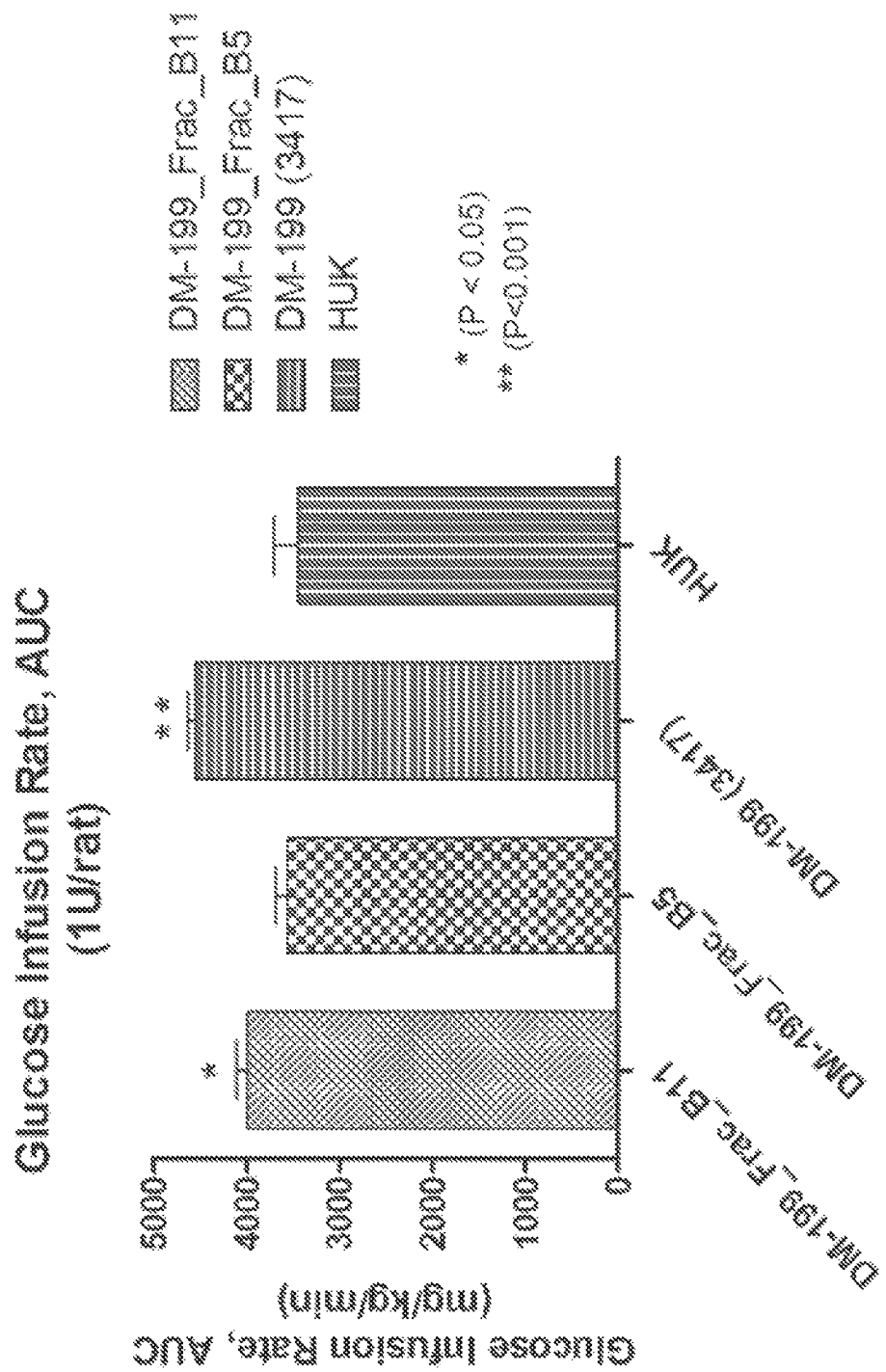
FIG. 8 is a graph of the area under the curve (AUC) of the glucose infusion rate in FIG. 7.

The rate of glucose infusion required to maintain equal blood glucose level was significantly higher with the groups treated with rhKLK1 (50:50 mixed glycoforms) at 1 U/rat than in animals treated with Fraction 11, Fraction 5, or HU KLK1. This difference is evident when the data is calculated a total AUC for the glucose infusion rate (see FIG. 8 and Table 4). For rats treated with fraction B11, the AUC is 3996+/−98 mg/kg/min-min (Mean+/−SEM) and for fraction B5, the AUC is 3551+/−113 mg/kg/min-min. It was expected that the 50:50 mixture of rhKLK1 would have an intermediate AUC between the low and high molecular weight glycoform. Surprisingly, for the 50:50 mixture, the AUC was 4547+/−69 mg/kg/min-min. This surprisingly high AUC indicates that the combination of the high and low molecular weight KLK1 has an unexpectedly additive or greater effect on stimulating glucose uptake. For the human urinary KLK1, since an equal amount of rhKLK1 and HU KLK1 was administered to the rats based on in vitro activity (Units calculated in the D-VLR-AFC assay), it was expected that the effect on GIR would be the same. However, the GIR AUC for human urinary KLK1 was 3444+/−227 mg/kg/min-min, which was significantly less than the 4547+/−69 mg/kg/min-min calculated for rhKLK1.

TABLE 4

Glucose Uptake

| Group/Dose | Compound | AUC GIR +/− SEM mg/kg/min · min |
|---|---|---|
| 1. 50:50 mixture 1 U/rat | rhKLK1 | 4547 +/− 69 |
| 4. High MW glycoform 1 U/rat | rhKLK1 fraction B11 | 3996 +/− 98 |
| 7. Low MW glycoform 1 U/rat | rhKLK1 fraction B5 | 3551 +/− 113 |
| 10. Urinary KLK1 1 U/rat | HU KLK1 | 3444 +/− 227 |

As shown in Table 5 below, the 50:50 mixture of rhKLK1 consistently stimulated increased glucose uptake in rats compared to HU KLK1 as measured by an increased AUC GIR. At a dose of 0.33 U, the rhKLK1 50:50 mixture AUC was 4127+/−78 mg/kg/min-min while HU KLK1 was 2969+/−144 mg/kg/min-min, and at 0.1 U, rhKLK1 was 3612+/−135 mg/kg/min-min while HU KLK1 was 2503+/−266 mg/kg/min-min.

TABLE 5

Glucose Uptake

| | AUC GIR +/− SEM mg/kg/min · min | |
|---|---|---|
| Dose | rhKLK1 50:50 | Urinary KLK1 |
| 1 U/rat | 4547 +/− 69 | 3444 +/− 227 |
| 0.33 U/rat | 4127 +/− 78 | 2964 +/− 144 |
| 0.1 U/rat | 3612 +/− 135 | 2503 +/− 266 |

In these experiments, equal amounts of KLK1 were administered into rats, based on the in vitro activity of KLK1 as measured in the protease assay. A single dose of KLK1 (double glycosylated isoform, triple glycosylated isoform, 50:50 mixture, or HU KLK1) was administered subcutaneously 30 minutes prior to clamp. Because the various KLK1 preparations were administered subcutaneously, the protein should be absorbed slowly into circulation relative to IV administration. Also, the animals were tested within 30 minutes of administration of the KLK1 polypeptides. As such, any differences in pK or half-life between the KLK1 polypeptides in circulation should be minimized and any effect on GIR should result from the activity of the administered KLK1.

Treatment of rats with the high molecular weight glycoform of rhKLK1 resulted in slightly increased glucose utilization, as detected in a greater AUC GIR, compared to low molecular weight glycoform of rhKLK1. This may in part be attributed to the high molecular weight glycoform having a longer half-life in circulation than the low molecular weight glycoform. The high molecular weight glycoform may not be cleared through the kidneys as readily. As discussed above, given the short timeframe for testing (30 minutes after administration), the effect may not be due solely to the half-life of the KLK1 protein in circulation.

Alternatively, the additional glycosylation may enable the higher molecular weight KLK1 glycoform to bind certain receptors in the animal, which could result in changes in glucose utilization. For example, the high molecular weight glycoform may be more efficient than the low molecular weight glycoform at stimulating a receptor directly, or bind another protein (eg serpin) more efficiently and the complex affects glucose utilization. The high molecular weight glycoform may also bind a receptor more efficiently that the low molecular weight glycoform, and sequester the KLK1 glycoform into a microenvironment where its enzyme activity acts to influence glucose utilization. The additional glycosylation may also allow the high molecular weight KLK1 glycoform to be more active in a physiological environment such as an animal, which is not reflected in the in vitro assays.

Surprisingly, the 50:50 mixture of glycoforms of rhKLK1 resulted in a greater AUC GIR compared to the high molecular weight glycoform. The expected result is the 50:50 mixed glycoforms would have an activity (as measured by AUC GIR) that is intermediate to the low- and high molecular weight glycoforms. This synergistic effect in the 50:50 mixture is unexpected. Indeed, the AUC GIR was significantly higher with the rats treated with rhKLK1 (50:50 mixture) compared to HU KLK1 (60:40 mixture) at all doses tested (sec Table 5).

One possible, non-limiting explanation for the synergy of the 50:50 glycoform mixture in the rats is that the high- and low-molecular weight glycoforms act in slightly different ways (slightly different enzyme activities, or slightly different binding to receptors) in a physiological setting. These slight differences in activities are complementary and thus synergistic when the glycoforms are in a 50:50 mixture. Alternatively, KLK1 may act through several difference mechanisms to influence glucose utilization, such as receptor binding and enzyme activity. The high- and low-molecular weight glycoforms may act in a complementary manner wherein one glycoform has higher enzyme activity in a physiological setting, while the other glycoform has higher binding affinity. Together, such differences result in a synergistic effect in an animal. This synergy or complementarity was not detected at the 60:40 ratio of high- to low-molecular weight KLK1.

A study was conducted in a type 2 diabetes animal model, specifically 11 week old db/db mice, administered the 52:57.5 mixture of rhKLK1 described previously. The db/db mice had developed type 2 diabetes as evidenced by fasting blood glucose levels greater than 250 mg/dl. The mice were separated into four groups of ten mice per group, and following an overnight (8 hour) fast, the mice were administered either buffer alone (negative control) or 2 Units, 0.8 Units or 0.04 Units per mouse of rhKLK1 mixture. 90 minutes after administration of the rhKLK1, the blood glucose levels in the mice was tested. In negative control animals, the blood glucose levels remained high 220+/−16 mg/dl. Animals receiving 2 Units rhKLK1 had a significant decrease in blood glucose levels to 141+/−9 mg/dl (p<0.05) compared to control. Animals receiving 0.8 Units per mouse had a less dramatic but still significant decrease in blood glucose levels to 149+/−14 mg/dl (p<0.05) compared to control. There was no statistical difference in blood glucose levels in mice receiving the lowest rhKLK1 dose of 0.04 Units per mouse (212+/−23 mg/dl) compared to control. Therefore, treatment of diabetic db/db mice with rhKLK1 at a glycoform ratio of 52:47.5 results in a significant decrease in the hyperglycemia.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

SEQUENCE FREE SEQUENCE LISTING

SEQ ID NO: 1-2 Amino acid sequences of human tissue kallikrein-1 preproprotein

What is claimed is:

1. A method of treating an ischemic condition in a subject in need thereof, comprising administering to the subject a composition comprising a first mature human tissue kallikrein-1 (KLK1) polypeptide and a second mature human tissue kallikrein-1 (KLK1) polypeptide:
   wherein the first mature human KLK1 polypeptide has three glycans attached at three different positions per said first mature human KLK1 polypeptide and the second mature human KLK1 polypeptide has two glycans attached at two different positions per said second mature human KLK1 polypeptide;
   wherein the three glycans of the first mature human KLK1 polypeptide are Asn-linked glycans at residues 78, 84, and 141 as defined by SEQ ID NO:1;
   wherein the two glycans of the second mature human KLK1 polypeptide are Asn-linked glycans at residues 78 and 84 but not 141 as defined by SEQ ID NO:1; and
   wherein the first mature human KLK1 polypeptide and the second mature human KLK1 polypeptide are present in the composition in a ratio ranging from about 45:55 to about 55:45.

2. The method of claim 1, wherein the ratio of first mature human KLK1 polypeptide and the second mature human KLK1 polypeptide in the composition is about 50:50.

3. The method of claim 1, wherein said mature human KLK1 polypeptide(s) comprise amino acid residues 78-141 of SEQ ID NO:1 or amino acid residues 78-141 SEQ ID NO:2.

4. The method of claim 1, wherein said mature human KLK1 polypeptide(s) comprise amino acid residues 25-262 of SEQ ID NO:1 or amino acid residues 25-262 of SEQ ID NO:2.

5. The method of claim 1, wherein said mature human KLK1 polypeptide(s) comprise an amino acid sequence having at least about 95% sequence identity to amino acid residues 25-262 of SEQ ID NO:1 or SEQ ID NO:2.

6. The method of claim 1, wherein said mature human KLK1 polypeptide(s) comprise an amino acid sequence having at least about 95% sequence identity to amino acid residues 25-262 of SEQ ID NO:2, and wherein said mature human KLK1 polypeptide(s) comprises E145 and/or A188.

7. The method of claim 1, wherein said mature human KLK1 polypeptide(s) comprise an amino acid sequence having at least about 95% sequence identity to amino acid residues 25-262 of SEQ ID NO:2, and wherein said mature human KLK1 polypeptide(s) comprises Q145 and/or V188.

8. The method of claim 1, wherein the mature human KLK1 polypeptide(s) comprises residues 25-262 of SEQ ID NO:1 or SEQ ID NO:2.

9. The method of claim 1, wherein the mature human KLK1 polypeptide(s) consists of amino acid residues 25-262 of SEQ ID NO:1 or amino acid residues 25-262 of SEQ ID NO:2.

10. The method of claim 1, wherein the composition comprises a pharmaceutically acceptable diluent, adjuvant, or carrier.

11. The method of claim 1, wherein the composition is substantially free of other glycosylated isoforms of KLK1.

12. The method of claim 1, where the composition has endotoxin levels of less than about 1 EU/mg protein, host cell protein of less than about 100 ng/mg total protein, host cell DNA of less than about 10 pg/mg total protein, and/or is substantially free of aggregates.

13. The method of claim 1, wherein greater than about 95% of the composition appears as a single peak by SEC HPLC.

14. The method of claim 1, wherein the ischemic condition is selected from brain ischemia (ischemic stroke), cardiac ischemia (myocardial ischemia), ischemic colitis, limb ischemia, and cutaneous ischemia.

* * * * *